US006420595B1

(12) United States Patent
Hallinan et al.

(10) Patent No.: US 6,420,595 B1
(45) Date of Patent: Jul. 16, 2002

(54) PROCESS CONTROL FOR VINYL ACETATE MANUFACTURE

(75) Inventors: Noel Hallinan, Cincinnati; Wayne Brtko, West Chester, both of OH (US)

(73) Assignee: Millennium Petrochemicals, Inc., Cincinnati, OH (US)

( * ) Notice: Subject to any disclaimer, the term of this patent is extended or adjusted under 35 U.S.C. 154(b) by 0 days.

(21) Appl. No.: 09/950,903

(22) Filed: Sep. 10, 2001

(51) Int. Cl.$^7$ .................. C07C 67/05; C07C 67/04; G01N 35/08; G01N 33/00
(52) U.S. Cl. ............... 560/245; 560/245; 560/242; 436/52; 436/139; 436/142
(58) Field of Search ............... 560/208, 261, 560/245, 243, 242; 436/52, 139, 142

(56) References Cited

U.S. PATENT DOCUMENTS 5,604,132 A * 2/1997 Capuano et al.
6,103,934 A * 8/2000 Hallinan et al.

* cited by examiner

Primary Examiner—Paul J. Killos
Assistant Examiner—Farhad Forohar
(74) Attorney, Agent, or Firm—Wood, Herron & Evans, LLP

(57) ABSTRACT

A method of real time process control in a reaction system for the production of vinyl acetate from the oxidation of ethylene and acetic acid. Reaction system samples are collected from the reactor vessel feed and/or effluent and/or from columns and/or transfer lines downstream of the reactor vessel, and the concentration of one or more components in the sample is measured by an infrared analyzer. The concentration measurements are then used to make adjustments in the concentration of components in the reaction system, directly or indirectly, such as by adjusting the temperature profile in a particular column, the flow rate of solution in to or out of a column, or the addition or extraction of a component to or from the solution. For optimum process control, the measurements are transmitted to a control unit for real time analysis, and the adjustments are made almost instantly after the infrared analysis.

22 Claims, 15 Drawing Sheets

PROCESS CONTROL FOR VINYL ACETATE MANUFACTURE

FIELD OF THE INVENTION

This invention relates to a method of improving process control in the manufacture and purification of vinyl acetate, and a method of manufacturing vinyl acetate utilizing improved process control.

BACKGROUND OF THE INVENTION

The prevailing method of vinyl acetate production is a vapor phase process involving continuously reacting ethylene, oxygen and acetic acid in a fixed bed catalyst reactor. The catalyst, generally palladium or a palladium/gold mixture is supported on a silica or alumina base. The two principal reactions that occur in the vinyl acetate process involve the reaction of ethylene, acetic acid and oxygen to form vinyl acetate and the undesired combustion of ethylene to form carbon dioxide and water. Other impurities formed in the production of vinyl acetate include acetaldehyde, ethyl acetate, methyl acetate, acetone, glycol diacetate, acrolein and crotonaldehyde.

The selectivity of the process and the percent conversion of the reactants are a function of several variables including reactor temperature, desired productivity and the condition of the catalyst. Deactivation of the catalyst, which routinely occurs over time due to buildup of tars and polymeric materials on the catalyst surface, can adversely affect the reaction process, particularly with regard to selectivity. These changes in reactor performance can ultimately lead to compositional changes in the liquid stream entering the purification section of a vinyl acetate plant.

In producing vinyl acetate, the reactor products of vinyl acetate, water and carbon dioxide are separated from the raw materials of ethylene and acetic acid, which are used in excess. The ethylene and acetic acid are recycled back to the reactor from the reaction and purification sections of the unit. Product vinyl acetate is recovered and purified in the purification section and sent to storage tanks. Wastewater is sent to a treatment facility and carbon dioxide is vented to a flare for disposal. Inert gases, such as nitrogen and argon, are typically purged from the reaction section to minimize buildup. These inert gases may or may not pass through an ethylene recovery unit installed to reduce loss of ethylene associated with the purge.

It is known to monitor the reactor feed and effluent by on-line gas chromatography and mass spectrometry. These on-line techniques are generally backed up by daily samples to cross check on-line analysis. Monitoring the reactor feed and effluent has a two-fold purpose. The first purpose is safety. The high flammability of ethylene and oxygen require that the feed composition be carefully monitored to ensure that the explosive limits are not exceeded. The second purpose is reactor performance. It is important to monitor the selectivity of the process and the percent conversion of the reactants, so that any adverse changes in these parameters can be quickly addressed.

A gas chromatograph (GC) can analyze the inlet and outlet reactor streams for carbon dioxide and ethylene. The carbon dioxide concentration is used to judge reactor performance and to calculate reactor selectivity. While this technique is adequate, it does have a number of drawbacks. A sample system is required to deliver the sample to the GC, and there is potential for chemical changes to occur in the sample transfer lines prior to analysis. Also, typically at least two separation columns must be used to separate the various stream components prior to GC analysis. A first column would typically be used to remove acetic acid and vinyl acetate from the sample. A second column would then be used to separate and quantify carbon dioxide and ethylene. Because of the need for a series of columns, typically a complete GC analysis requires at least fifteen minutes or so leading to a significant time lag between real time composition and measured composition. Thus, measurements are generated infrequently, and the number of hardware items involved in the analysis increases the potential for maintenance.

A mass spectrometric analyzer can be used to determine the percent composition of reactor feed and effluent components. As in the case of gas chromatography, a complex sample system is required to deliver the sample to the analyzer, resulting in infrequent measurements, and the potential for chemical changes occurring in the sample lines, incomplete sample delivery, and other related problems.

Persons skilled in the art of vinyl acetate processing are aware that undesired cycling or pulsing of reactor inlet and outlet component concentrations can occur. This cyclic behavior would generally be in response to downstream upsets that cause such pulsing to occur in recycle streams that feed the reaction system. An example would be a cyclic variation in the temperature of the primary tower bottoms recycle to the reaction section. Depending on the cycle frequency, it is possible that this undesired behavior will go undetected with an inadequate frequency of analysis, such as the time frame of fifteen minutes or greater achievable with gas chromatographic analysis and mass spectrometric analysis.

On-line infrared spectroscopy has been used for characterizing and quantifying components of a chemical process gas or liquid stream. For example, the use of on-line infrared analysis in controlling reactor liquid composition in the acetic acid process has been described in U.S. Pat. No. 6,103,934 entitled MANUFACTURING AND PROCESS CONTROL METHODS and U.S. patent application Ser. No. 09/611,067 filed Jul. 6, 2000 and entitled MANUFACTURING AND PROCESS CONTROL METHODS. The advantages of infrared spectroscopy in analysis of an acetic acid manufacturing process downstream of the reactor were discussed in copending U.S. patent application Ser. No. 09/672,893 filed Sep. 29, 2000 and entitled PROCESS CONTROL FOR ACETIC ACID MANUFACTURE. The use of on-line infrared analysis as described in Ser. No. 09/672,893 provided real time process control of component concentrations in a reaction system for producing acetic acid.

Similar to the manufacturing process for acetic acid, production and purification of vinyl acetate requires removal of other components from the vinyl acetate product and, where necessary, to either recycle these other components (acetic acid, water, ethyl acetate, acetaldehyde, polyvinyl acetate, ethylene and carbon dioxide) to the reactor or other parts of the process, or send these other components to waste with minimum product or raw material loss. The composition of these purification streams will partially be a function of reaction section performance and partially a function of purification section column performance. There is thus a need to implement process control via on-line infrared analysis in the reaction system for the production of vinyl acetate.

SUMMARY OF THE INVENTION

The present invention provides a method of real time process control of component concentrations in a reaction system for the production of vinyl acetate from the oxidation of ethylene and acetic acid. To this end, and in accordance with the present invention, samples of reaction system solution are collected from the reactor vessel feed and/or effluent and/or from columns and/or transfer lines downstream of a reactor vessel, and the concentration of one or more components in the sample is measured by an infrared analyzer. The concentration measurements are used to make adjustments in the process. The concentration of one or more components is adjusted, either directly or indirectly, in one or more locations in the reaction system in response to the measurements. For example, the flow rate of a solution stream in a transfer line can be increased or decreased going into or out of a column to alter the concentration of one or more of the components in that column or another vessel in the reaction system. Alternatively, the temperature of the solution in a column or stream or the temperature profile or gradient in a column could be increased or decreased to affect the concentration of one or more components in the reaction system solution. Also, the concentration of a reaction system component can be adjusted by direct addition or extraction of that component into or out of the solution. For example, acetic acid concentration in the reaction system can be adjusted either directly by increasing or decreasing the acetic acid feed into the acid tower that feeds the reactor vessel, or indirectly by increasing or decreasing recycle stream flow rates containing acetic acid to the reaction section. Thus, reaction system component concentrations can be adjusted directly or indirectly by varying any number of process variables in the reaction system. Further, adjustment in one location of the reaction system may cause concentration changes at either that location or upstream or downstream of that location. For optimum process control, the measurements are transmitted to a control unit for real time analysis, and the adjustments are made almost instantly after the infrared analysis. There is thus provided a method for continuously updating the conditions of the reaction system to enhance process control in real time of the overall process to thereby optimize the production and purification of vinyl acetate product.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

Because nearly every asymmetric molecule has an infrared spectrum, infrared spectroscopy is generally capable of characterizing every molecular component of a chemical process stream. The advantages of infrared spectroscopy in analysis of a vinyl acetate reactor sample are two-fold. A heated near-infrared gas probe could be directly inserted into reactor inlets and outlets, thus eliminating the need for a sample system. This ensures that the measured concentrations are optimally representative of the actual concentrations in the stream being measured, a distinct advantage over the above-described gas chromatographic and mass spectrometric methods. Secondly, the sensitivity achievable in the near-infrared method means that frequency of analysis could be of the order of one minute or less. This more frequent monitoring of acetic acid, ethylene, vinyl acetate and carbon dioxide in the reactor inlet and outlet will allow an enhanced fine-tuning of reactor performance to optimize selectivity and percent conversion.

Infrared spectroscopy also offers advantages in analysis of a sample downstream of the reactor, in either another portion of the reaction section or in the purification section. Changes in temperature and composition in any stream or column within the reaction system can cause a rippling effect of change throughout other portions of the reaction system both upstream and downstream of that stream or column. Availability of frequent analysis of streams and columns throughout the plant can allow powerful algorithmic relationships to be developed towards optimizing reactor and purification operations.

To understand the operation and benefits of real time process control of the reaction system for vinyl acetate in accordance with the present invention, it is deemed necessary to describe generally the vinyl acetate reaction system, including the various potential columns and streams in a manufacturing plant and how they interact to produce the final vinyl acetate product.

A. The Vinyl Acetate Reaction System

Figure 1:
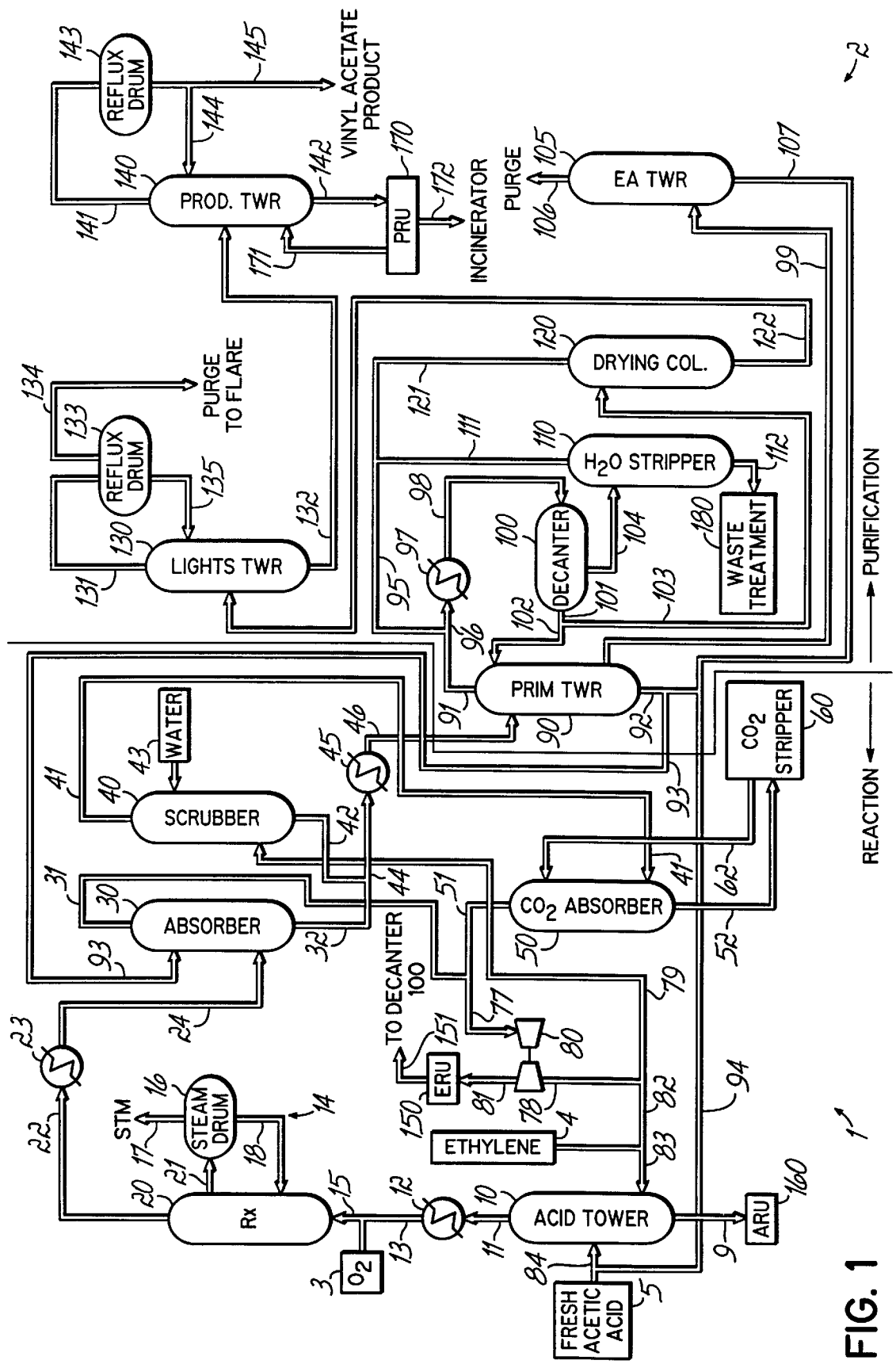
FIG. 1 is a schematic representation of a vinyl acetate manufacturing plant.

A vinyl acetate manufacturing plant practicing vapor phase production of vinyl acetate by the reaction of ethylene, acetic acid and oxygen over a fixed bed catalyst is depicted schematically in FIG. 1. While the reaction system can be conveniently divided into two functional areas, the reaction section 1 and the purification section 2, such division is not necessary for purposes of discussing the present invention. Thus, the entire process will generally be referred to throughout as the reaction system. The vinyl acetate system may vary in the type and number of absorbing columns, scrubbing columns, drying towers, etc., for example as described in U.S. Pat. Nos. 3,404,177, 3,438,870 and 4,156,632, which are within the skill of one of ordinary skill in the art, and which are included in the scope of this invention.

In general, the reaction system includes an acid tower 10 with an overhead stream 11 which is heated in reactor feed heater 12. Heated stream 13 is the reactor hydrocarbon feed prior to addition of oxygen 3. After the oxygen addition, the resulting mixed feed stream 15 feeds the reactor 20 and the exothermic heat of reaction is removed by a reactor coolant system 14. The reactor coolant system 14 includes a steam drum 16 from which low pressure steam is generated. Reactor coolant liquid under pressure, stream 21, flows from reactor 20 to steam drum 16 where steam 17 flashes at about 25 psig. The remaining liquid stream 18 plus make-up water (not shown) is returned to the reactor 20 by a coolant pump (not shown). The initial reactor product stream 22 is cooled in the reactor effluent cooler 23 and the resulting cooled reactor product stream 24 feeds directly a vinyl acetate absorber column 30 and indirectly a scrubber column 40 and a carbon dioxide absorber column 50. Crude product stream 32 from the absorber bottom and crude product stream 42 from the scrubber bottom combine as stream 44, which is heated in feed heater 45. The heated feed stream 46 feeds the remainder of the reaction system which generally includes a primary tower 90, a phase separation vessel (decanter) 100, ethyl acetate tower 105, a water stripper column 110, a drying column 120, a lights tower 130 and a product tower 140. Transfer lines, such as pipes, through which process gases and liquids flow, connect columns and vessels. For ease of depiction and discussion, the transfer lines and gas and/or liquid therein are referred to herein as one and the same, using the term "stream." For further ease of depiction and discussion, it should be understood that process liquids are transferred by means of pumps, though such pumps are not depicted in the figures.

More specifically, the feed stream 15 to the reactor 20 comes from the overhead stream 11 of the acid tower 10. The purpose of the acid tower 10 is two-fold. First, the tower 10 is used as a means of mixing the two main reactants, ethylene and acetic acid, in the correct ratio before sending them to the reactor 20 and second, to purify the acetic acid used in the process. This purification is accomplished in the multiple tray distillation portion (detail not shown) of the acid tower 10. This distillation removes heavy impurities contained in the recycled acetic acid from the primary tower 90 bottom (discussed below). The gas feed stream 83 to the acid tower 10 consists of the recycle gas stream 82 and fresh ethylene 4. This combined gas feed stream 83, which consists mainly of ethylene, but contains some oxygen, water, carbon dioxide and inert gases, enters at a low point of the acid tower 10. The liquid feed stream 84 to the acid tower 10 consists of fresh acetic acid 5 and combined stream 94 from a portion of the bottoms stream 92 of the primary tower 90 and the bottoms stream 107 of the ethyl acetate tower 105. This liquid feed stream 84 thus consists of about 70 to 95% acetic acid and the remainder water. It is fed to the acid tower 10 at a higher point than the gas recycle stream 83. The up-flowing gas from stream 83 contacts the down-flowing liquid from stream 84, which saturates the ethylene with the amount of acetic acid required for proper reactor feed preparation.

The acid tower overhead stream 11 is comprised mainly of ethylene saturated with acetic acid and contains oxygen along with some water, carbon dioxide and inert gases. This overhead stream 11 is heated by steam in the reactor feed heater 12 to a temperature matching the inlet coolant temperature of the reactor 20. Heated stream 13 either feeds a single reactor 20 or is split in half if two reactors (20) are present. Fresh oxygen 3 is injected into the reactor feed stream 13. The actual concentration of oxygen will vary between well-defined limits depending on the catalyst activity. The resulting reactor feed stream 15 enters at the bottom of the reactor 20 and flows upward through catalyst-packed tubes (not shown) in the reactor 20. There is a small pressure drop through these tubes. In the reactor 20, the vapor phase reactants (ethylene, oxygen and acetic acid) are partially converted to vinyl acetate and small amounts of byproducts. It should be noted that an excess of acetic acid and a large excess of ethylene are used versus a theoretical concentration ratio of 2:1:2 for ethylene/oxygen/acetic acid. An excess of acetic acid is required to serve as diluent to reduce or eliminate the risk of forming an explosive mixture, as well as to limit the formation of byproduct carbon dioxide. An excess of ethylene is required both from an explosive mixture standpoint as well as a means of controlling the velocity of feed stream 15 through the catalyst tubes. It is important to avoid overheating in the reactor 20 because, aside from affecting the yield of reactants to vinyl acetate product and causing deposition of tars and polymer, destruction of the catalyst will occur. If the conversion to carbon dioxide becomes excessive, the large amount of heat liberated can cause the catalyst to become overheated and damaged. For these reasons, it is important that the correct reactant velocity is maintained, as well as maintaining proper reactor cooling, specified ratios of ethylene, oxygen and acetic acid and correct reactor temperature and pressure. The reaction to form vinyl acetate as well as the reaction to form carbon dioxide are exothermic, and to control the reaction temperature, the heat of reaction must be removed from the reactor 20. This is accomplished with the reactor coolant system 14.

The initial reactor effluent stream 22 from the reactor 20 is cooled and partially condensed in the reactor effluent cooler 23 before flowing via stream 24 to the absorber column 30, or simply referred to as the absorber 30. The purpose of the absorber 30 is to remove the product vinyl acetate and most of the unreacted acetic acid from the reactor effluent stream 24, prior to recompressing for recycle back to the reactor 20. The reactor effluent stream 24 enters the absorber 30 below the bottom tray therein (not shown) where the gas flows up through the trays countercurrent to a predominantly acetic acid stream 93 which is fed to the absorber 30 from the primary tower 90. This aqueous acetic acid stream 93 absorbs all of the vinyl acetate product and most of the unreacted acetic acid from the reactor 20. The absorber bottoms stream 32 containing crude vinyl acetate product and acetic acid is fed toward the primary tower 90 (discussed later) and the absorber overhead stream 31, containing non-condensable gases (carbon dioxide, ethylene, oxygen etc.) saturated in acetic acid, is fed to the recycle gas compressor 80 through stream 77.

The recycle gas compressor 80 pressures up the recycle gas stream 82 in order to return it through the acid tower 10 back to the reactor 20. It is beneficial to maintain a reaction section ethylene concentration of at least 60 mole percent to enhance the selectivity toward vinyl acetate in the reactor 20. This is typically accomplished in either of the following two ways. A slipstream of the high pressure discharge from the recycle compressor 80 can be purged to a flare to reduce process impurities. While this method may have been accepted in the past, today the corresponding loss of expensive ethylene raw material is unacceptable. This led to the development of ethylene recovery units for impurity reduction. In this case, a portion of the high pressure recycle gas from recycle gas compressor 80, as stream 81, feeds the ethylene recovery unit 150 to remove impurities without a significant ethylene loss. At the same time, ethylene concentration in the reaction section is also kept high to maintain selectivity at the desired level in the reactor 20.

Slipstream 79 is taken from the recycle gas compressor discharge stream 78 and is fed to scrubber 40. The purpose of the scrubber 40 is to remove the residual acetic acid in this slipstream 79. The slipstream 79 enters the scrubber 40 below the bottom tray therein (not shown) and the gas flows up through the trays countercurrent to a stream of demineralized water 43. Demineralized water 43 removes virtually all of the acetic acid from the slipstream 79. The scrubber bottoms stream 42 is pumped toward the primary tower 90 for recovery of the acetic acid. Scrubber bottoms stream 42 is fed toward the primary column 90 along with the bottoms stream 32 from the absorber 30, as stream 44. Stream 44 is heated by feed heater 45, and the resulting heated stream 46 is fed to primary tower 90. The overhead or off-gas stream 41 from the scrubber 40 consisting primarily of ethylene, carbon dioxide, argon, nitrogen and oxygen is routed to a carbon dioxide absorber 50.

The goal of the carbon dioxide absorber 50 is to remove carbon dioxide from the gas stream 41 being recycled to reactor 20. This is accomplished by use of a carbonate absorption process, which converts the carbon dioxide produced in the reactor to potassium bicarbonate, which is then regenerated to potassium carbonate in a carbon dioxide stripper 60. More specifically, the carbon dioxide absorber bottoms stream 52 is sent to the carbon dioxide stripper 60, the purpose of which is to regenerate the rich carbonate content of carbon dioxide absorber bottoms stream 52 from the carbon dioxide absorber 50 of the reactor train by removing the carbon dioxide. Potassium bicarbonate is broken down to potassium carbonate with the liberation of carbon dioxide and water, which go overhead to flare from the carbon dioxide stripper 60. The lean carbonate bottoms stream 62 from the stripper 60 is returned to the top of the carbon dioxide absorber 50. The recycle feed to the carbon dioxide absorber 50 is from the scrubber overhead stream 41. The feed enters below the bottom tray therein (not shown), where it flows up through the tower and contacts the lean carbonate bottoms stream 62 passing down through the trays. The potassium carbonate in the lean carbonate bottoms stream 62 reacts with, and removes almost half of the carbon dioxide present in the gas stream 41. The recycled gas stream 51, now greatly reduced in carbon dioxide concentration, leaves the top of the carbon dioxide absorber 50 and joins overhead stream 31 from absorber 30 to make stream 77, which is the feed to recycle gas compressor 80.

The feed stream 46, consisting mainly of vinyl acetate, acetic acid and water, which come from the bottoms of the scrubber 40 and absorber 30 towers after heating by feed heater 45, enters the primary tower 90. The purpose of the primary tower 90 is to separate vinyl acetate, water and other light components from acetic acid. Vinyl acetate along with water approaching the vinyl acetate-water azeotrope is taken overhead as stream 91. The primary tower bottoms stream 92 consists of about 70% to about 95% acetic acid and is pumped back to the absorber 30 via stream 93 and to the acid tower 10 in the reaction section via stream 94. Sidedraw stream 99 is taken from a tray in primary tower 90 and fed to ethyl acetate tower 105. Middle boiling ethyl acetate is purged as overhead stream 106 and aqueous acetic acid is returned via stream 107 to combine with a portion of the primary tower bottoms stream 92 for recycling back to acid tower 10 via combined stream 94.

The purpose of the decanter 100 is two-fold. It is a reflux drum and a holdup drum to allow the condensed liquid feed stream 98 to separate into two phases. The solubility of water in the vinyl acetate phase stream 101 and vinyl acetate in the water phase stream 104 is temperature dependent and increases with temperature. The upper phase stream 101 is primarily vinyl acetate with a couple of percent water and the lower phase stream 104 is primarily water with a couple of percent vinyl acetate. Excess acetic acid in the decanter 100 should be avoided, as it will inhibit the phase separation. The vinyl acetate upper phase stream 101 is removed from the decanter 100 by a reflux pump (not shown), which returns most of the stream 101 back to the primary tower 90 as reflux stream 102 while the remainder of stream 101 is fed to the drying column 120 via stream 103. The lower water phase stream 104 is pumped to the water stripper 110. The water stripper 110 separates the small amount of vinyl acetate from the water. The water stripper overhead stream 111, comprised mainly of vinyl acetate, combines with the drying column overhead stream 121 and the mixture is stream 95. The wastewater in the bottoms stream 112 is fed to the waste treatment system 180.

The drying column 120 strips out the small amount of water dissolved in the vinyl acetate phase stream 103. The water with some vinyl acetate goes overhead as stream 121. As stated above, water stripper overhead stream 111 and drying column overhead stream 121 combine as stream 95. Stream 95 is recycled and joins the primary tower overhead stream 91 to form stream 96. Stream 96 is condensed in condenser 97 and resulting condensate stream 98 is fed to decanter 100. The dry vinyl acetate from the bottoms stream 122 is pumped to the lights tower 130.

The objective of the lights tower 130 system is to separate light impurities from vinyl acetate. The light impurities removed consist mainly of acetaldehyde, methyl acetate, acrolein, acetone and ethanol. These impurities are separated overhead in the lights tower overhead stream 131 and reflux drum 133 and then stream 134 is purged to flare from reflux drum 133. The purified bottom stream 132 from lights tower 130 is then fed to the product tower 140. In this tower 140, final product vinyl acetate is taken overhead from the heavy impurities to reflux drum 143. The overhead product 145 is collected into storage tanks. The bottom stream 142 from the product tower 140 is then processed in the product recovery unit (PRU) 170. The PRU 170 produces a bottom product stream 172, which has a higher polymer concentration (e.g., polyvinyl acetate) than does the product tower bottoms stream 142. The PRU bottoms stream 172 also serves as a purge for other heavy waste such as ethyl acetate. The overhead product from the PRU is returned to the product tower 140 via stream 171 and the PRU bottoms product stream 172 is disposed of by incineration.

Hydroquinone, for example, is used as an inhibitor of vinyl acetate polymerization in the primary tower 90, lights tower 130 and product tower 140 and in the vent gas compressor (not shown). The final vinyl acetate product in stream 145 contains a trace concentration of the polymerization inhibitor to prevent polymerization occurring during storage and shipment.

B. Process Control in the Vinyl Acetate Reaction System

1. Flow, Level, Temperature and Pressure Control

The general method of plant control is based on level and flow control throughout the reaction system. Temperature control is used to minimize energy requirements and to maintain product specifications. Both on-line and off-line analysis is employed to monitor the stream compositions for guidance and warning.

The reactor feed stream 15 is from the acid tower overhead stream 11 and a flow control valve (not shown) is used to adjust the flow rate into reactor 20. Controlling the acid tower overhead pressure with make up fresh ethylene 4 sets the desired reactor inlet pressure. The oxygen flow 3 to the reactor feed stream 13 is a function of acid tower overhead 11 flow and catalyst activity. The reactor coolant system 14 is used to control reaction temperature as the feed rate is varied.

As an excess of acetic acid and ethylene are used in the reactor feed 15, the recovery and return of these components to the reaction section 1 is of critical importance. This is further complicated by the presence of byproduct carbon dioxide, which must be removed to prevent buildup in the reaction section 1. Various temperature, pressure, level and flow controls in the purification section 2 allow relatively clean recycle streams to return to the reaction section 1 and allow in-spec product to enter storage tanks. By "in-spec," it is meant that the vinyl acetate product contains at or below the specified maximum concentrations for impurities as specified by the purchaser of the product. Similarly, by "off-spec," it is meant that the vinyl acetate product contains impurities at a concentration that exceeds the maximum allowable amount. The effluent stream 24 from the reactor 20 flows to the absorber 30. The recycle acid stream 93 which is part of the primary tower bottoms stream 92 and which is used to absorb vinyl acetate, is fed to the absorber 30 on flow control. The absorber bottoms 32 containing vinyl acetate (5–40%), acetic acid and water is pumped on level control to the primary tower 90. The operating pressure of the absorber 30 is tied to the acid tower overhead pressure and to the pressure drop in the system. The overhead or off-gas stream 31 from the absorber 30 is fed to recycle gas compressor 80. A slipstream 79, after being compressed, is returned as feed to scrubber 40. The purpose of the scrubber 40 is to remove acetic acid from the slipstream 79 and prevent corrosion of the carbon dioxide absorber 50. Demineralized water 43 used to scrub out the acetic acid is fed to the scrubber 40 on flow control. Scrubber bottoms stream 42 on level control is pumped to the primary tower 90 along with the absorber bottoms 32 for recovery of acetic acid. The overhead or off-gas 41 from the scrubber 40 is fed to the carbon dioxide absorber 50.

The lean carbonate bottoms stream 62 from the carbon dioxide stripper 60 to the top tray (not shown) of the carbon dioxide absorber 50 is flow controlled. Make-up potassium hydroxide required in the system is fed on a continuous basis to replenish potassium lost in the blowdown of the carbon dioxide absorber 50 bottoms. Absorber 50 is also equipped with a level controller with both a high and a low-level alarm on the rich carbonate in the bottoms stream 52.

Essentially pure acetic acid 5 and combined stream 94 from a portion of the primary tower bottoms stream 92 and the ethyl acetate tower bottoms stream 107 are fed as stream 84 containing about 70% to about 95% acetic acid in water to a tray of the acid tower 10 on flow control. A liquid level controller based on the level in the acid tower 10 bottoms resets the feed flow. The gas feed stream 83 to the acid tower 10 consists of the recycle gas stream 82 from the recycle compressor 80 and fresh ethylene 4. The ethylene to acetic acid ratio in the acid tower overhead stream 11 is a known function of overhead temperature and pressure.

The primary tower 90 is central to the operation of the purification section 2 and to the recycle of the bottom stream 92 to the reaction section 1. Feed stream 46 to the primary tower 90 is on flow control reset by absorber 30 and scrubber 40 bottoms levels. After separation of vinyl acetate, water and other light components from acetic acid, a portion of the recovered acid in primary tower 90 is recycled as stream 93 back to the absorber 30 on flow control and the remainder of the recovered acid is recycled as stream 94 to the acid tower 10 at a flow rate based on acid tower 10 bottoms level. The temperature of the primary tower 90 bottoms is controlled to maintain the desired level of acetic acid in the bottoms stream 92.

A profile of ethyl acetate is established in the primary tower 90 based on temperature. At the point of high ethyl acetate concentration, a slipstream 99 is removed and fed to ethyl acetate tower 105. Ethyl acetate is purged from the system in overhead stream 106, and aqueous acetic acid is returned to primary tower bottom stream 92 as stream 107 for recycling to the acid tower via combined stream 94.

The overhead stream 91 of the primary tower 90 is sent to the decanter 100 after condensation. The two liquid phases in the decanter 100 are under level control. Part of the vinyl acetate upper phase stream 101 is pumped to the top of the primary tower 90 via reflux stream 102 and part is fed via stream 103 to the drying column 120. The lower water phase stream 104 is pumped on level control to the water stripper 110. The stripper bottoms stream 112, consisting primarily of waste water, is pumped on local level control through the waste water cooler (not shown) to the waste treatment system 180.

The drying column bottoms stream 122 is pumped on level control to the lights tower 130. The lights tower 130 bottoms has a pre-set upper pressure limit. Because the lights tower 130 is essentially on total reflux, the reboil rate sets the internal reflux in the tower 130. The product stream 132 from the lights tower 130 is taken on level control from the tower bottoms and is pumped to the product tower 140. The overhead stream 131 from the lights tower 130 is condensed and collected in a reflux drum 133. The reflux drum 133 is on level control with a small purge stream 134 taken to the flare based on pressure control.

The product tower 140 is equipped with a product recovery unit (PRU) 170 which concentrates the polymer (e.g., polyvinyl acetate) and other heavy impurities in the bottom purge stream 142 from the product tower 140. A slipstream of the product tower bottoms 142 is taken by flow control to the PRU flash heater to allow recovery of the vinyl acetate content via stream 171 back to the product tower 140.

2. Composition Control

The concepts of flow, level, temperature and pressure control work reasonably well in ensuring quality control. Nevertheless, compositional changes may occur that may lead to undesirable conditions in the process. Since some of these compositional changes may not be detected in a timely fashion by normal control methods, it would be appreciated by one skilled in the art of vinyl acetate manufacture that continuous updates of component concentrations of various streams and columns would greatly benefit optimum operation of the reaction system. Furthermore, a continuous update of reactor 20 and acid tower 10 component concentrations would allow reactor operation to be optimized such that catalyst deactivation can be decelerated.

Typically, and as has already been discussed, reactor 20 inlet and outlet analysis is carried out by on-line gas chromatographic and mass spectrometric analysis. While these are adequate analytical techniques, the hardware is problematic in that both methods of analysis require a sample slipstream being delivered to the analyzer. Those skilled in the art of on-line process analysis will appreciate that building and maintaining a liquid sample delivery system to an analyzer is considerably more complex and prone to frequent maintenance than the analysis itself. This complexity is further increased when delivery of a vaporized sample is required, as is the case in analysis of the vinyl acetate reactor 20. The current invention inserts a heated infrared gas probe directly into the reactor 20 inlet and outlet, thus alleviating the need for a sample delivery system.

Analysis of the reaction system vessels and streams is typically conducted by off-line sampling followed by laboratory analysis of some of these streams. These samples are obtained a few times daily and generally there is a lag of several hours between sampling and the stream composition data becoming available to plant operators. Also, while this off-line data helps in determining average performances of vessels, it does not give information on any possible cyclic behavior in the vessels of interest. For example, uneven performance of the carbon dioxide absorber 50 can lead to significant and detrimental concentrations of carbon dioxide returning in the recycle gas stream 83 to the acid tower 10 and hence to the reactor 20 where dilution of feedstock will impact performance. Such cyclic or uneven behavior might be invisible to infrequent daily sampling but will be readily apparent from continuous on-line data in accordance with the present invention.

Another example of the failure of off-line data to provide information on cyclic behavior would be the propensity for vinyl acetate polymerization in the absence of adequate concentrations of hydroquinone polymerization inhibitor in the purification section 2. Real time monitoring of polymer concentration (e.g., polyvinyl acetate) at several locations will allow any potential build up of polymer deposits to be recognized and addressed.

Yet another example is control of the lights tower 130. Off-line control is based primarily on lab analysis of the product stream 132 and overhead purge stream 134. Set points on the reboil steam flow control and blowdown of the lights tower reflux drum 133 are established to maintain concentrations of methyl acetate in the lights tower bottoms stream 132 and acrolein in the purge stream 134. The acrolein in the purge stream 134 could be conveniently and accurately monitored on-line to aid in column control.

3. Process Control of Individual Equipment a. Reactor

Desired operation of reactor 20 involves preferential oxidation of ethylene and acetic acid to vinyl acetate rather than oxidation of ethylene to combustion products, carbon dioxide and water. For this reason, optimal operation of a vinyl acetate plant requires that the selectivity and percent conversion be tied to acid tower overhead stream 11 flow rate and composition. Thus any discussion of reactor 20 performance also encompasses acid tower 10 performance. Infrared gas probes inserted directly into the reactor inlet and outlet lines would allow the vinyl acetate/acetic acid/carbon dioxide/ethylene ratios to be determined. These ratios in and out of the reactor 20 allow the selectivity of the process to vinyl acetate formation and the percent conversion of acetic acid and ethylene to be directly measured. As both selectivity and percent conversion are closely linked to catalyst age and activity, their intrinsically dynamic nature as determined by the infrared measurements can be used to tune reactor temperature and reactor feed 15 composition such that selectivity and percent conversion are optimized. Maintaining selectivity and percent conversion within a narrow range will allow the downstream purification and recycle sections to operate close to steady state as reactor effluent 22 composition will be close to invariant. It will also permit operation of reactor feed in the safe range as far as explosive oxygen limit, while still maximizing vinyl acetate production.

b. Absorber/Scrubber

The absorber 30 is the first step toward recovery of crude vinyl acetate and unreacted ethylene from reactor effluent 24. The temperature of the acetic acid aqueous solution stream 93 used as absorbent is optimally cool or basically at the temperature achievable with cooling water. Stream 93 is flow-controlled to maximize the recovery of crude vinyl acetate. While sufficient flow for the stream is necessary for absorption and scrubbing of the condensable compounds, excess flow must be avoided to minimize energy requirements.

Scrubber 40 removes residual acetic acid from stream 79. Demineralized water 43 scrubs out acetic acid and protects the carbon dioxide removal unit. The bottom stream 32 from absorber 30 is combined into stream 44 with scrubber 40 bottom stream 42 and preheated in feed heater 45 prior to being fed as stream 46 to the primary tower 90. The heat is provided by cross-exchange (not shown) in feed heater 45 with the stream 93 portion of the primary tower 90 bottoms stream 92. Excess flow of either acetic acid aqueous solution 93 or demineralized water 43 can exceed the heating capability of the feed heater 45. This in turn would put an additional load on primary tower 90 that must be heated by the primary tower steam reboiler (not shown). The key is to minimize water in the feed to primary tower 90 because any excess must be boiled and taken overhead with the vinyl acetate, thereby increasing the energy required. However, it is also important to not overheat primary tower feed stream 46 because overheating can generate free radicals that will lead to problems with polymerization in downstream equipment.

Insertion of near-infrared probes in the absorber 30 and scrubber 40 bottom streams 32 and 42, respectively, would assist in optimizing operation of these two towers. For example, if the water concentration in the absorber bottoms 32 approached 15 wt. %, either the acetic acid aqueous solution 93 or the demineralized water 43 could be reduced. The near-infrared probes would also provide a forewarning about concentration upsets that must be dealt with downstream. Impurities, such as acetaldehyde, acrolein, acetone, methyl acetate and ethyl acetate, must be reduced by downstream purification equipment. If these compounds are monitored by probes in the absorber 30 and scrubber 40 bottom streams 32 and 42, higher than desired concentrations could be identified early and assist in operation of downstream equipment to achieve vinyl acetate product that meets established purity specifications. An example of this would be to begin increasing the reboiler duty of the lights tower 130 to drive impurities overhead in preparation for the higher than desired impurities observed by the upstream probes.

c. Carbon Dioxide Removal Unit

Scrubber 40 and the carbon dioxide removal unit (including absorber 50 and stripper 60) are on a slipstream from recycle gas compressor 80. Removal of the carbon dioxide generated in the reactor 20 is important for maintaining a material balance in the reaction section 1. If not purged from the process, carbon dioxide would continue to accumulate and certainly at some level affect the performance of the reactor 20. Typically, the carbon dioxide removal unit, which includes carbon dioxide absorber 50 and stripper 60, successfully accomplishes this task. This absorption process uses potassium carbonate in the carbon dioxide absorber 50 to convert carbon dioxide to potassium bicarbonate, which is regenerated to potassium carbonate in the carbon dioxide stripper 60. Carbon dioxide flow from the carbon dioxide stripper 60 overhead is monitored for confirmation of removal.

While feed 41 to the bottom of the carbon dioxide absorber 50 is simply based on the desired hydrocarbon circulation rate in the reaction section, stream 62 is rich in potassium carbonate and is flow-controlled to the top of the tower 50. Guidelines are established for potassium carbonate and potassium bicarbonate concentrations in the carbon dioxide absorber bottoms stream 52 representative of proper operation of the carbon dioxide removal unit. For example, potassium carbonate content ranges from about 1 to 4 wt. % and potassium bicarbonate content ranges from about 20 to 25 wt. % in the absorber bottoms stream 52. Potassium acetate is an undesired byproduct in the removal process caused by carryover of vinyl acetate or acetic acid in upstream equipment. While this warning of carryover is valuable, the potassium acetate also inhibits absorption of carbon dioxide and is corrosive. For this reason, potassium acetate is typically blown down from the carbon dioxide absorber bottom stream 52 to keep its concentration below 4 wt. % in the stream 62. This also results in a loss of both potassium carbonate and bicarbonate. Potassium hydroxide is added to stream 62 to makeup for potassium lost as potassium acetate, carbonate and bicarbonate or as potassium metal compounds in the blowdown.

Infrared analysis of the carbon dioxide absorber bottoms stream 52 would assist in decisions regarding blowdown of the absorber bottoms for potassium acetate control. Proper adjustment would minimize potassium hydroxide makeup. An infrared gas probe installed in the carbon dioxide stripper overhead line (not shown) would give a faster indication of the carbon dioxide content in the off-gas to assist in improving performance of the removal unit. A lower than expected carbon dioxide removal rate would guide one to verify the flow rate and the potassium carbonate and bicarbonate compositions of lean carbonate stream 62 or the performance of the cross-exchangers (not shown) that cool stream 62.

d. Ethylene Recovery Unit (ERU)

Feed to the ethylene recovery unit 150 is supplied as a slipstream 81 from the recycle gas compressor 80. In the absence of this unit 150, purging to the atmosphere is required to maintain ethylene concentration and impurity levels in the reaction section. As a raw material cost reduction, the concept of ethylene recovery from the purge was developed to reduce fresh ethylene usage. Typically, the feed stream 81 is fed to the recovery unit 150 in which ethylene is absorbed by a vinyl acetate stream (not shown) and recycled via stream 151 to the primary tower condenser 97 and then to decanter 100. The remaining vapor stream (not shown) vented from the unit 150 contains a fraction of the original ethylene and provides the path for economical impurity removal.

Monitoring ethylene in the slipstream 81 feeding this unit 150 and in the waste vent stream (not shown) by infrared will allow optimization of the recovery unit 150 operation. Buildup of impurities in the feed stream 81 would lead to absorption and recycle of these impurities to the primary tower condenser 97. This would increase the load on the vent gas compressor (not shown). At some point, the impurity level would require venting to the flare to purge the impurities from the process.

e. Acid Tower

The liquid feed stream 84 to the acid tower 10 consists of fresh acetic acid 5 and combined stream 94 from a portion of the bottom stream 92 of the primary tower 90 and bottom stream 107 from the ethyl acetate tower 105. A major purpose of the acid tower 10 is to purify acetic acid before it is fed to the reactor 20. This is achieved by a multi tray distillation section (not shown) of the acid tower 10, which serves to remove heavy impurities. A profile of this section of the acid tower 10 would allow its efficiency to be monitored and tuned to optimize removal of heavies. Thus, as in the case of the primary tower 90, near-infrared probes could be inserted at various trays for real time analysis of acetic acid, water and heavies such as glycol diacetate and polyvinyl acetate. The gas feed stream 83 to the acid tower 10 consists of the recycle gas stream 82 from the recycle compressor 80 and fresh ethylene 4. The combined gas stream 83 consists mainly of ethylene but contains some oxygen, water, carbon dioxide and inert gases. All components other than oxygen and inert gases are amenable to analysis by an in-situ infrared gas probe. The combined information on gas stream 83 and liquid stream 84 feeds to the acid tower 10 can be used to determine appropriate operating temperatures and pressures. The carbon dioxide content of the acid tower inlet gas stream 83 will also be an indicator of the efficiency of the carbon dioxide absorber 50 and could be used to optimize the concentrations of potassium carbonate and bicarbonate in stream 52 from the carbon dioxide absorber 50.

f. Acid Recovery Unit (ARU)

The bottom stream 9 from the acid tower 10 still contains an equilibrium amount of acetic acid with the heavy impurities. A portion of this stream 9 is purged to remove the heavies but a loss of some acetic acid still incurs. Recovery of this acetic acid has value and for this reason, the acid recovery unit 160 was developed. This unit 160 contains a recovery tower operating at vacuum to separate the acetic acid from the undesirable heavy impurities. Insertion of an infrared probe in the remaining liquid stream would provide information on the loss of acetic acid in the bottom waste stream (not shown) from the unit 160 and aid in optimization of operation of the ARU 160 to minimize acetic acid loss. This would also reduce the quantity of material in the bottom waste stream and thereby reduce the waste disposal cost.

g. Primary Tower and Ethyl Acetate Tower

The objective of primary tower 90 is to separate the vinyl acetate from raw material acetic acid. The vinyl acetate is taken overhead with water and other impurities that are removed in the purification process. Acetic acid is recovered in the bottom of primary tower 90 for recycle. Conditions where continuous updates of the component concentrations in the primary tower 90 are useful to process control are outlined below.

The primary tower 90 is operated with liquid filled trays (not shown). Insertion of near-infrared probes at various trays would allow a concentration profile to be made of the column 90. Typically, it is desired to keep about 70% to about 95% acetic acid in the primary tower bottoms stream 92. Under normal operating conditions this ensures that little or no acetic acid goes in the primary tower overhead stream 91 to the decanter 100. As acetic acid is miscible with both vinyl acetate and water, the presence of significant concentrations of acetic acid in the decanter 100 would lead to incomplete or no phase separation. The resultant increase in water in the vinyl acetate phase stream 101 could lead to overloading of the drying column 120 and the increase in vinyl acetate in the water phase stream 104 could lead to vinyl acetate exiting the water stripper 110 via bottoms stream 112 to waste. An acetic acid/water profile of the primary tower 90 could be used to tune the temperature in the primary tower bottoms stream 92 to maintain the desired component ratio.

Near-infrared probes could also permit an ethyl acetate concentration profile in primary tower 90. This information could be used to identify the location of high ethyl acetate concentration where the sidedraw 99 should be taken to feed ethyl acetate tower 105.

The water balance around the primary tower 90 is a function of the tower performance itself and also a function of the bottoms feed stream 46 from the absorber 30 and scrubber 40 and the overhead return 95 from the water stripper 110 and drying column 120. The absorber and scrubber bottoms 32 and 42 are combined as stream 44, heated in heater 45 and fed to the primary tower 90 via stream 46. A near-infrared probe may be inserted into the primary tower feed lines 44 or 46 to monitor the acetic/water ratio. This ratio may vary significantly during startups after catalyst regeneration when the whole system is water rich and when significant off-spec product may be made. The primary tower feed composition from stream 46 as measured by the infrared probe could be used during transitional periods to avoid unduly high levels of water in the feed to the purification section 2. Thus, the yield of in-spec product during these transitional periods would be optimized, and so would the energy usage in primary tower 90.

An infrared profile of the primary tower 90 would also allow a profile of polymer concentration to be determined. Higher than normal levels of polyvinyl acetate could indicate a problem with the polymerization inhibitor injection system (not shown) or inadequate concentration of polymerization inhibitor. Again, the polymerization inhibitor injection rate could be tuned to a real time infrared measurement of polymer concentration. Finally, the infrared profile would also allow the vinyl acetate and light impurity compositions to be determined. The measured concentrations of light impurities (e.g., acetaldehyde, acetone, acrolein and methyl acetate) could be used in determining optimal operation of the lights tower 130 where these light impurities go overhead to flare via stream 134.

h. Decanter

A probe inserted in both phases of the decanter 100 could be used to monitor acetic acid concentration. Thus any potential phasing problems that might develop due to rising concentration of acetic acid could be identified and quickly addressed. Similar to the primary tower 90, light impurities and polyvinyl acetate could also be measured. In effect, a decanter probe could be used as a cross-check of performance of a primary tower probe and vice versa. Additionally, analysis of the compositions of the two phases as a function of decanter temperature would help to guide operation toward the best split. While lower temperature favors the separation so that there is less vinyl acetate in the water phase stream 104 and less water in the vinyl acetate phase stream 101, there is a cost associated with lower temperature. Using near-infrared analysis to frequently determine the compositions of the two phases would quantify the separation as a function of temperature so that the most economical operation can be chosen.

i. Drying Column

Water is taken overhead with an equilibrium amount of vinyl acetate in drying column 120 and crude vinyl acetate is recovered in the bottom stream 122. On-line infrared analysis of drying column feed stream 103, bottom stream 122 and overhead stream 121 for water, vinyl acetate and polyvinyl acetate content will allow operation of the drying column 120 to be optimized. The feed stream 103 to the drying column 120 is the vinyl acetate rich phase stream 103 from the decanter 100. The goal of the drying column 120 is to reduce the water content in the bottom crude product stream 122. Overhead stream 121 should approach the vinyl acetate-water azeotrope. Knowledge of the concentrations of compounds in the streams around the drying column 120 would assist in optimal operation of the column 120 from both a purity and energy viewpoint.

j. Lights Tower

Lights tower 130 separates light impurities, such as acetaldehyde, methyl acetate, acrolein and acetone, from the crude vinyl acetate in bottom stream 122 from drying tower 120. The overhead stream 131 from the lights tower 130, which is condensed and collected in a reflux drum 133, contains predominantly vinyl acetate with light impurities. A probe in this drum 133 would allow continuous analysis of these impurities. The impurities present and their relative concentrations could be diagnostic of lights tower performance, especially since the overhead purging via stream 134 of impurities also involves a loss of vinyl acetate. Basically there is a trade-off between loss of vinyl acetate and pushing impurities back down the tower 130. Insertion of an infrared probe in liquid on the trays (not shown) within the lights tower 130 would give a more rapid indication of movement of impurities down the tower 130 and potentially time to compare the economics of one option versus the other. The goal is to achieve a bottom stream 132 that is essentially free of water and light impurities.

k. Product Tower

The product tower 140 is the final opportunity to produce in-spec vinyl acetate product 145. The feed stream 132 has already been dried via column 120 and light impurities have essentially been removed via lights tower 130, leaving vinyl acetate with heavy impurities. Unfortunately, one of these impurities is ethyl acetate, which boils closely to vinyl acetate. This separation requires a tower with many trays to achieve the in-spec vinyl acetate product. Monitoring ethyl acetate and any residual light impurities with infrared probes in the condensed overhead product stream 145 from reflux drum 143 and in the liquid on the trays in the tower 140 would assist in optimal operation of the product tower 140. Information obtained by infrared probes installed in upstream equipment would also warn of upsets that could result in higher than desired concentrations of impurities in product tower 140. If these light impurities reach the light tower bottom stream 132, they will surely be in vinyl acetate product stream 145. Early warning would guide operation of upstream equipment to minimize light impurities in product tower feed stream 132.

l. Product Recovery Unit (PRU)

Product recovery unit 170 was designed to recover desirable vinyl acetate from the bottom waste stream 142 of product tower 140. The bottom stream 142 from the product tower 140 is an equilibrium mixture of ethyl acetate and vinyl acetate containing heavy impurities. A portion of the stream 142 is fed to the product recovery unit 170 for recovery of vinyl acetate. The unit 170 contains a flash to separate vinyl acetate from the heavy impurities with recycle of the flash vapor to the product tower 140 via stream 171. An infrared probe inserted into the heavy waste stream 172 would monitor loss of vinyl acetate and provide information for improved recovery of vinyl acetate in the recovery unit 170.

C. Calibration Modeling

Infrared calibration models were obtained using chemometric techniques as described in U.S. Pat. No. 6,103,934 and U.S. patent application Ser. No. 09/611,067, expressly incorporated by reference herein in their entirety. Chemometrics is a branch of chemical analysis utilizing statistics wherein algorithmic relationships and mathematical logic are incorporated to obtain a calibration model involving multi-variate analysis. The term multi-variate analysis refers to the relation of the concentration of a component in a solution to many infrared wavelengths or frequencies. Software products are commercially available which permit ready application of chemometric techniques. Representative products include PIROUETTE™, from Infometrix, Seattle, Wash. The general steps involved in developing chemometric calibration models are well known to those skilled in the art. Also, the American Society for Testing and Materials (ASTM) has published a document titled "Standard Practices for Infrared Multivariate Analyses (No. E1655-94)", incorporated herein by reference in its entirety, in which recommended guidelines are provided.

To obtain a good chemometric calibration model it is important to properly choose the calibration standards. A large number of calibration standards may need to be prepared and analyzed where there is a broad weak signal for the component of interest which is overlapped with signals from other components. The number can be in the range of 30 to 300. To create an accurate calibration model, a number of calibration standards are prepared, each containing all of the components normally present in the reaction system solution. Some or all of these components are to be eventually analyzed by infrared spectroscopy. The components of individual standards are independently varied by concentration to randomize any bias or interferences that one component might have on another. The maximum and minimum concentration values expected in the reaction system solution serve as the boundary limits for the individual component concentrations. After the standards are prepared they are sequentially injected into the infrared analyzer and a spectroscopic signal is collected. Generally, the individual spectra for the calibration standards are first converted into digitized format and then set up in a spreadsheet with the corresponding concentrations of the component which is to be measured. Partial Least Squares (PLS) regression methods are then used to fit the data.

Figure 2B:
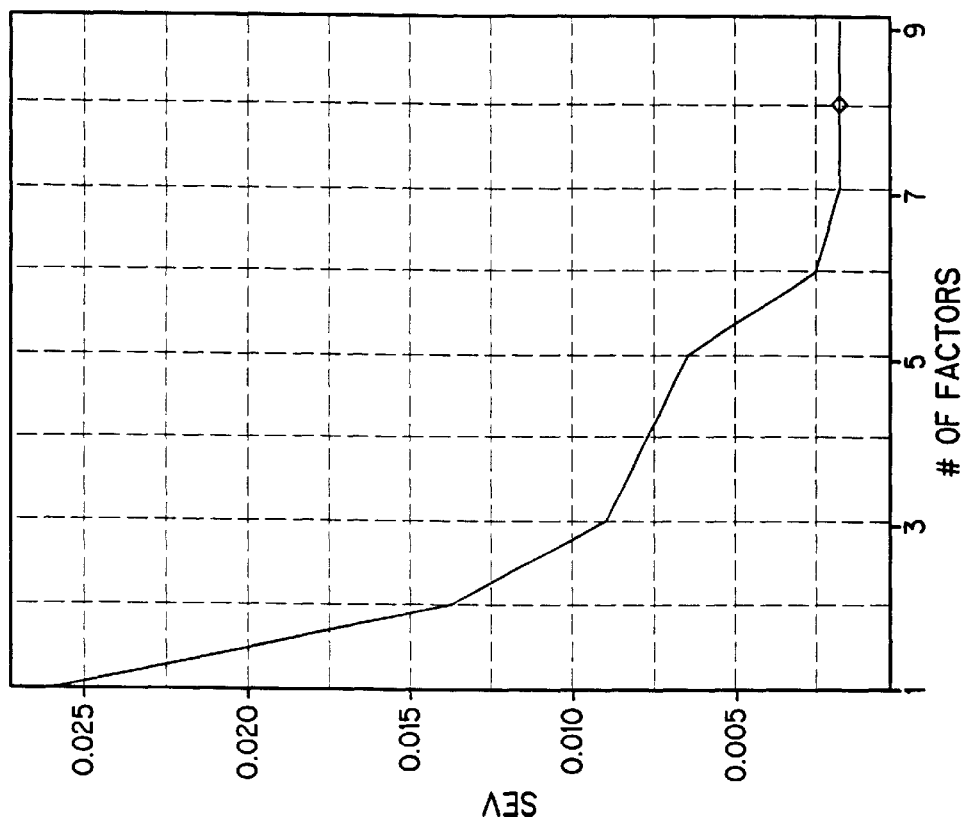
FIGS. 2A–2B are a calibration curve and a corresponding SEV plot, respectively, for a vinyl acetate calibration model.
Figure 2A:
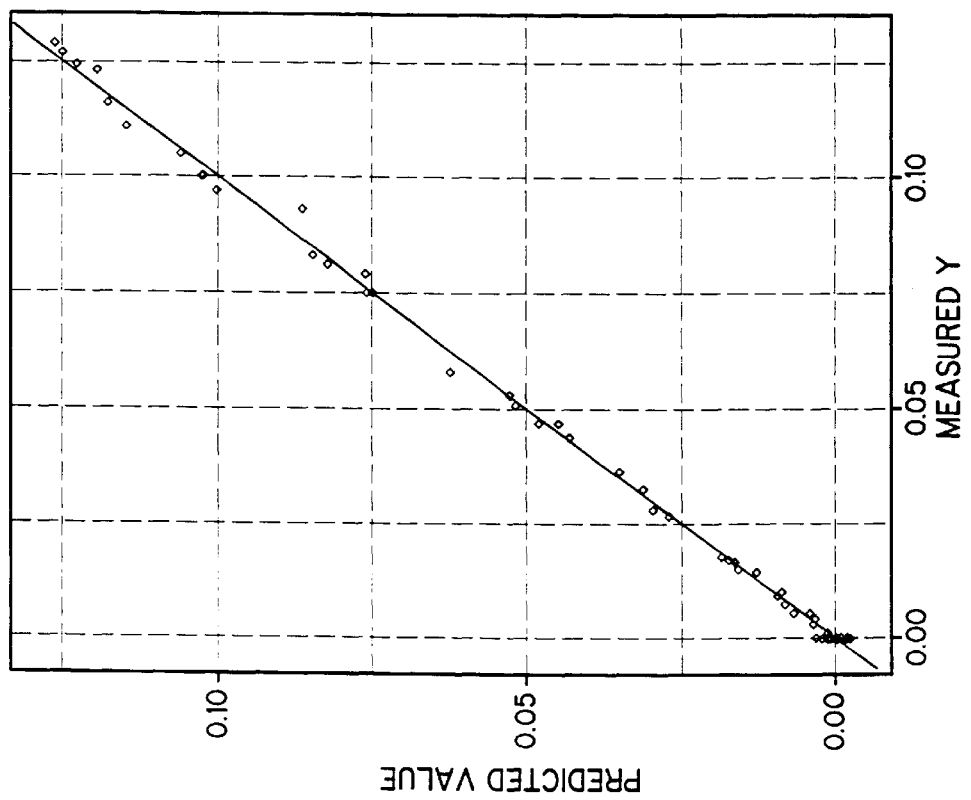

Statistical tests used to evaluate and optimize calibration models obtained from data fitting are automatically run by the software during the PLS regression. In one of these tests, called cross validation, one sample from the calibration set is temporarily left out and the remaining samples are used to create a model. From this model, a prediction is made of the component concentration associated with the left-out sample and the residual (difference between actual and predicted) recorded. Another sample is then excluded, a new model is made and a new prediction and residual are generated. The procedure is repeated until every sample has been left out once. A resulting plot of the standard error of cross variance (SEV) against number of factors allows the optimal number of factors to be included in the model to be identified. This optimal number is associated with the minimum error in the SEV. An example of this is shown in FIGS. 2A and 2B. FIG. 2A shows the calibration curve obtained for vinyl acetate in the gas phase and FIG. 2B shows the corresponding SEV plot where it is indicated that eight factors were used to obtain the calibration curve in FIG. 2A.

The spectral regions used in obtaining calibration models for each component in the extended mid-infrared are shown in Tables 1 and 2 for liquid and gas phase components respectively. It is well known to those skilled in the art of spectroscopy that the first overtone bands in the extended mid-infrared region (4000 cm$^{-1}$ to 7000 cm$^{-1}$) have corresponding second and third overtone bands in the near-infrared region which incorporates the extended mid-infrared region and stretches from approximately 4000 cm$^{-1}$ to 12500 cm$^{-1}$. Approximately an order of magnitude decrease in intensity occurs on going from first to second overtone and on going from second to third overtone. Thus, any of the overtone bands in the near-infrared could be used for quantitative analysis by modifying the cell or probe pathlength.

TABLE 1

Extended Mid-Infrared
(using 0.5 mm pathlength fiber optically coupled probe)
Spectral Regions Used for Quantitative Analysis of Liquids in Vessels and Streams

| Vessel | Component | Spectral Region (cm$^{-1}$) |
|---|---|---|
| Primary Tower | Glycol Diacetate | 6160–5890, 5280–5000, 4840–4440 |
|  | Acetaldehyde | 5990–5640, 5200–4450 |
|  | Water | 5400–4980 |
|  | Acetic Acid | 5340–5195, 4790–4405 |
|  | Vinyl Acetate | 6350–5600, 5500–4250 |
|  | Polyvinyl Acetate | 6275–5890, 5400–4340 |
|  | Ethyl Acetate | 6250–5800, 4600–4400 |
| Lights Tower Condensed Samples & Reflux Drum | Acetone | 6100–5480, 4850–4470 |
|  | Acrolein | 6225–5720, 5420–4630 |
|  | Acetaldehyde | 6300–5530, 5260–5020, 4750–4475 |
|  | Ethanol | 6030–5840, 5180–4800 |
|  | Vinyl Acetate | 6300–5880 |
|  | Methyl Acetate | 6140–5635, 4675–4300 |
| Product Tower | Vinyl Acetate | 6280–5270, 4900–4760 |
|  | Ethyl Acetate | 6100–5780, 4600–4300 |
|  | Acetic Acid | 4700–4450 |
|  | Hydroquinone | 6100–5820, 5050–4580 |
|  | Polyvinyl Acetate | 6900–5800, 4780–4300 |
| Absorber/Scrubber | Water | 5990–4540 |
|  | Acetic Acid | 5370–4560, 5990–5680 |
|  | Vinyl Acetate | 6300–5580, 5500–4240 |
| Decanter Heavy Phase | Water | 5550–4450 |
|  | Acetaldehyde | 6200–5670, 4830–4500 |
|  | Acetic Acid | 4700–4350 |
|  | Vinyl Acetate | 6300–5580, 4850–4600 |
| Decanter Light Phase | Water | 5300–4850 |
|  | Acetaldehyde | 6200–5300, 5100–4550 |
|  | Acetic Acid | 4900–4300 |
|  | Vinyl Acetate | 6300–5300, 4950–4660 |

TABLE 2

Extended Mid-Infrared
(using 100 mm pathlength gas transmission cell)
Spectral Regions Used for Quantitative Analysis of Reactor Inlet and Effluent Gases

| Gas (or vapor phase of liquid) | Spectral Regions (cm$^{-1}$) |
|---|---|
| Ethylene | 6420–5530, 5175–4200 |
| Carbon Dioxide | 5230–4700 |
| Vinyl Acetate | 6300–5580, 5530–4200 |
| Acetic Acid | 7000–6690, 5490–4200 |
| Water | 5590–4490 |

It should be noted that the appropriate spectral region used for quantitatively analyzing a particular component may vary depending on the vessel or stream in which it is being analyzed, given that a particular component may be more concentrated at one location in the reaction system as compared to its concentration at another location. This can be seen in Table 1, where, for example, water is measured in the extended mid-infrared region of 5550–4450 cm$^{-1}$ in the decanter heavy phase and in the extended mid-infrared region of 5300–4850 cm$^{-1}$ in the decanter light phase.

For each liquid stream or vessel to be simulated to create calibration models, multi component solutions were prepared to obtain the spectroscopic data. Concentration ranges for these solutions were consistent with the ranges examined in the individual on-line examples detailed herein. Because of the complexity of preparation of multi component gas mixtures, each gas component was modeled separately. For ethylene, various pressures ranging from one atmosphere to three atmospheres were introduced to the gas cell and infrared spectra recorded at each pressure. The concentration at each pressure was then calculated from the ideal gas equation referred to below. For each experiment at a particular starting pressure, the temperature was also varied. While the concentration of ethylene remained unchanged with temperature, as the volume is fixed, spectral changes may result. Thus, spectra for fixed concentrations of ethylene at different temperatures were incorporated into the calibration model for ethylene. For carbon dioxide, weighed amounts of dry ice (solid carbon dioxide) were quickly added to the gas cell through the ball valve. Over several minutes the dry ice would completely sublime to gaseous carbon dioxide. At this point infrared spectra were recorded. Similarly to ethylene, the temperature was varied for each carbon dioxide concentration.

Vapor pressure curves for room temperature liquids in gas phase experiments were obtained from the open literature. Vapor pressure data for acetic acid were obtained from "Chemical Engineer's Handbook", 5th edition (1973). Vapor pressure data for vinyl acetate were obtained from "Trans. Electro. Chem. Soc., 63, 425 (1933). Vapor pressure data for water were obtained from "Thermodynamic Properties of Water including Vapor, Liquid and Solid Phases," Keenan, Keyes, Hill & Moore, Wiley (1969). These vapor pressure curves allowed the calculation of vapor phase concentrations at different temperatures using the ideal gas equation. This equation, well known to those skilled in the art of vapor phase chemistry and vinyl acetate processing is shown below:

$$PV=nRT$$

where P refers to the gas pressure in atmospheres (atm), V refers to the gas volume in liters (L), T refers to the temperature in Kelvin (K), n refers to the number of moles of gas and R is the ideal gas constant, 0.082 atm·L·mol$^{-1}$K$^{-1}$. While it is well known to those skilled in the art of vapor phase chemistry, and while it is appreciated herein that the ideal gas equation, when solved for n, provides only an approximation of the number of moles in the gas phase due to non-ideality not accounted for in the ideal gas equation, nevertheless overall trends in vapor phase behavior with changes in temperature generally correlate with values of n predicted by the ideal gas equation. Thus, for the purposes of the gas phase experiments described herein where the feasibility of such quantitative gas analysis is addressed, no correction for non-ideal behavior is made.

In individual experiments, known quantities of acetic acid, water and vinyl acetate, which are all liquids at room temperature, were each added to the gas cell and the gas cell heated in increments up to about 120° C. for vinyl acetate and up to about 180° C. for acetic acid and water to increase the vapor phase fraction. Infrared spectra were recorded at intermediate temperatures and the concentrations (n moles of gas) of vinyl acetate, water and acetic acid in the vapor phase at each temperature were calculated from the ideal gas equation.

Figure 3:
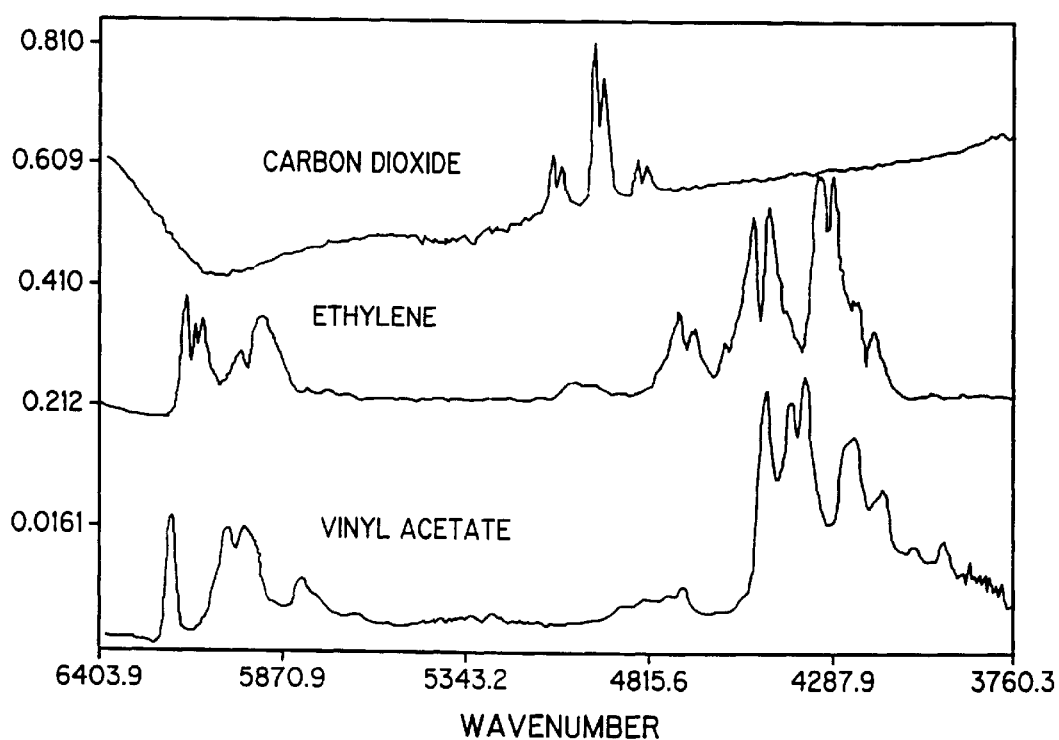
FIG. 3 is on-line extended mid-infrared spectra for carbon dioxide, ethylene and vinyl acetate.

An example of gas phase infrared spectra is shown in FIG. 3 where spectra of carbon dioxide, ethylene and vinyl acetate gas samples were obtained separately. To maximize the accuracy of the gas calibration models and to avoid false positive readings, the individual calibration models for each component contained the spectra for all other components with zero concentration values inputted.

Validation of all models was carried out in which solutions of known composition were prepared, infrared spectra obtained and concentrations predicted using the calibration models. Validation data for decanter heavy and light phases are shown in Tables 3 and 4, respectively. Validation data for purification lights tower/reflux drum liquid samples are shown in Table 5. Validation data for primary tower top and bottoms type solutions are shown in Tables 6 and 7, respectively. Validation data for product tower bottoms type solutions are shown in Table 8. Validation data for absorber bottoms type solutions are shown in Table 9, and validation data for reactor inlet and outlet gas samples are shown in Table 10. Correlation coefficients (R factors) of 0.995 or greater associated with the values in Tables 3–10 indicate a high degree of accuracy for analysis of all components.

TABLE 3

Accuracy of Extended Mid-Infrared Calibration Models for Decanter Heavy Phase Type Solutions

| Sample No. | Water (Molar) | | Vinyl Acetate (Molar) | | Acetic Acid (Molar) | | Acetaldehyde (Molar) | |
|---|---|---|---|---|---|---|---|---|
| | Actual | Predict | Actual | Predict | Actual | Predict | Actual | Predict |
| 1 | 55.03 | 54.94 | 0 | 0.009 | 0.174 | 0.192 | 0 | 0.007 |
| 2 | 52.97 | 53.16 | 0.050 | 0.063 | 0.709 | 0.730 | 0.205 | 0.240 |
| 3 | 51.01 | 50.99 | 0.172 | 0.164 | 1.100 | 1.041 | 0.054 | 0.072 |
| 4 | 48.92 | 49.04 | 0.320 | 0.350 | 1.661 | 1.726 | 0.150 | 0.149 |
| 5 | 46.06 | 46.11 | 0.477 | 0.511 | 1.955 | 2.046 | 0.309 | 0.312 |

TABLE 4

Accuracy of Extended Mid-Infrared Calibration Models for Decanter Light Phase Type Solutions

| Sample No. | Water (Molar) | | Vinyl Acetate (Molar) | | Acetic Acid (Molar) | | Acetaldehyde (Molar) | |
|---|---|---|---|---|---|---|---|---|
| | Actual | Predict | Actual | Predict | Actual | Predict | Actual | Predict |
| 1 | 0 | 0.007 | 10.70 | 10.79 | 0.08 | 0.14 | 0.205 | 0.239 |
| 2 | 0.051 | 0.060 | 10.41 | 10.46 | 0.71 | 0.67 | 0 | 0.030 |
| 3 | 0.190 | 0.184 | 10.02 | 9.97 | 0.92 | 0.99 | 0.401 | 0.411 |
| 4 | 0.456 | 0.478 | 9.74 | 9.74 | 1.57 | 1.65 | 0.103 | 0.091 |
| 5 | 0.899 | 0.924 | 9.52 | 9.58 | 1.60 | 1.69 | 0.304 | 0.287 |

TABLE 5

Accuracy of Extended Mid-Infrared Calibration Models for Purification Lights Tower Condensed Type Samples and Reflux Drum Type Samples

| Sample No. | Ethanol (Molar) | | Vinyl Acetate (Molar) | | Methyl Acetate (Molar) | | Acrolein (Molar) | | Acetone (Molar) | | Acetaldehyde (Molar) | |
|---|---|---|---|---|---|---|---|---|---|---|---|---|
| | Actual | Predict | Actual | Predict | Actual | Predict | Actual | Predict | Actual | Predict | Actual | Predict |
| 1 | 0 | 0.013 | 7.99 | 8.07 | 1.10 | 1.05 | 0.79 | 0.75 | 0.12 | 0.12 | 2.02 | 1.96 |
| 2 | 0.029 | 0.033 | 9.04 | 8.91 | 1.48 | 1.55 | 0.40 | 0.41 | 0.08 | 0.09 | 0.24 | 0.21 |
| 3 | 0.078 | 0.084 | 6.02 | 6.04 | 3.73 | 3.71 | 0.55 | 0.55 | 0 | 0.02 | 1.90 | 1.88 |
| 4 | 0.144 | 0.132 | 5.40 | 5.51 | 4.70 | 4.66 | 0.62 | 0.60 | 0.29 | 0.28 | 1.02 | 0.97 |
| 5 | 0.348 | 0.325 | 6.74 | 6.70 | 0.56 | 0.51 | 2.24 | 2.18 | 0.17 | 0.18 | 2.66 | 2.52 |

TABLE 6

Accuracy of Extended Mid-Infrared Calibration Models for Primary Tower Top Type Solutions

| Sample No. | Vinyl Acetate (Molar) | | Water (Molar) | | Acetic Acid (Molar) | | Acetaldehyde (Molar) | | Glycol Diacetate (Molar) | | Polyvinyl Acetate (Wt %) | |
|---|---|---|---|---|---|---|---|---|---|---|---|---|
| | Actual | Predict | Actual | Predict | Actual | Predict | Actual | Predict | Actual | Predict | Actual | Predict |
| 1 | 10.42 | 10.49 | 0.61 | 0.55 | 0 | 0.03 | 0.54 | 0.49 | 0 | 0.020 | 0 | 0.140 |
| 2 | 9.81 | 9.77 | 0.22 | 0.19 | 0.83 | 0.88 | 0.10 | 0.09 | 0.042 | 0.066 | 0.204 | 0.249 |
| 3 | 9.09 | 9.08 | 0 | 0.02 | 2.40 | 2.32 | 0.25 | 0.27 | 0.322 | 0.294 | 0.555 | 0.533 |
| 4 | 8.48 | 8.52 | 1.40 | 1.45 | 3.06 | 3.07 | 0 | 0.03 | 0.157 | 0.165 | 0.329 | 0.365 |
| 5 | 8.15 | 8.18 | 1.84 | 1.83 | 3.23 | 3.29 | 0.33 | 0.36 | 0.091 | 0.102 | 0.481 | 0.507 |

TABLE 7

Accuracy of Extended Mid-Infrared Calibration Models for Primary Tower Bottom Type Solutions

| Sample No. | Vinyl Acetate (Molar) | | Water (Molar) | | Acetic Acid (Molar) | | Acetaldehyde (Molar) | | Glycol Diacetate (Molar) | | Polyvinyl Acetate (Wt %) | |
|---|---|---|---|---|---|---|---|---|---|---|---|---|
| | Actual | Predict | Actual | Predict | Actual | Predict | Actual | Predict | Actual | Predict | Actual | Predict |
| 1 | 0.10 | 0.05 | 7.11 | 7.05 | 14.05 | 14.11 | 0.32 | 0.36 | 0.30 | 0.33 | 0.61 | 0.56 |
| 2 | 0.55 | 0.58 | 4.53 | 4.43 | 14.73 | 14.66 | 0.16 | 0.18 | 0.09 | 0.12 | 0.21 | 0.19 |
| 3 | 2.20 | 2.24 | 5.66 | 5.66 | 10.77 | 10.78 | 0 | 0.04 | 0.61 | 0.6 | 0.13 | 0.17 |
| 4 | 2.73 | 2.62 | 3.93 | 3.88 | 11.65 | 11.67 | 0.21 | 0.22 | 0 | 0.01 | 0.35 | 0.38 |
| 5 | 3.24 | 3.23 | 3.20 | 3.14 | 9.19 | 9.24 | 0.24 | 0.26 | 0.79 | 0.82 | 0.05 | 0.13 |

TABLE 8

Accuracy of Extended Mid-Infrared Calibration Models for Product Tower Bottoms Solutions

| Sample No. | Vinyl Acetate (Molar) | | Ethyl Acetate (Molar) | | Hydroquinone (Molar) | | Acetic Acid (Molar) | | Polyvinyl Acetate (Wt %) | |
|---|---|---|---|---|---|---|---|---|---|---|
| | Actual | Predict | Actual | Predict | Actual | Predict | Actual | Predict | Actual | Predict |
| 1 | 8.50 | 8.55 | 2.15 | 2.05 | 0.023 | 0.020 | 0.071 | 0.078 | 0.00 | 0.13 |
| 2 | 2.22 | 2.16 | 8.23 | 7.90 | 0.042 | 0.039 | 0.102 | 0.114 | 1.01 | 0.92 |
| 3 | 5.18 | 5.22 | 5.16 | 5.06 | 0 | 0 | 0.146 | 0.155 | 0.32 | 0.40 |
| 4 | 6.13 | 6.15 | 4.30 | 4.23 | 0.085 | 0.074 | 0.080 | 0.084 | 0.77 | 0.81 |
| 5 | 4.12 | 4.15 | 6.21 | 6.13 | 0.061 | 0.054 | 0 | 0.023 | 0.51 | 0.56 |

TABLE 9

Accuracy of Extended Mid-Infrared Calibration Models for Water, Vinyl Acetate and Acetic Acid in Absorber Bottoms Type Solutions

| Sample No. | Water (Molar) | | Vinyl Acetate (Molar) | | Acetic Acid (Molar) | |
|---|---|---|---|---|---|---|
| | Actual | Predict | Actual | Predict | Actual | Predict |
| 1 | 5.68 | 5.69 | 0 | 0 | 15.71 | 15.68 |
| 2 | 11.32 | 11.38 | 0.75 | 0.77 | 12.72 | 12.68 |
| 3 | 0 | 0.02 | 2.31 | 2.35 | 13.78 | 13.70 |
| 4 | 3.07 | 3.04 | 1.18 | 1.17 | 14.63 | 14.60 |
| 5 | 8.51 | 8.53 | 1.77 | 1.80 | 11.97 | 11.91 |

TABLE 10

Accuracy of Extended Mid-Infrared Calibration Models for Reactor Inlet and Outlet Gas Phase Type Samples

| Sample No. | Temperature (° C.) | Vinyl Acetate (Molar) | | Acetic Acid (Molar) | | Ethylene (Molar) | | Carbon Dioxide (Molar) | | Water (Molar) | |
|---|---|---|---|---|---|---|---|---|---|---|---|
| | | Equation | Predict | Equation | Predict | Equation | Predict | Equation | Predict | Equation | Predict |
| 1 | 50 | 0 | 0.0011 | 0.0027 | 0.0035 | 0 | 0.0011 | 0 | 0.0016 | 0 | 0.0004 |
| | 70 | 0 | 0.0014 | 0.0065 | 0.0079 | 0 | 0.0014 | 0 | 0.0006 | 0 | 0.0001 |
| | 90 | 0 | 0.0009 | 0.0141 | 0.0133 | 0 | 0.0014 | 0 | 0.0018 | 0 | 0 |
| | 110 | 0 | 0.0007 | 0.0242 | 0.0261 | 0 | 0.0016 | 0 | 0.0008 | 0 | 0 |
| 2 | 30 | 0.0074 | 0.0091 | 0 | 0.0006 | 0 | 0 | 0 | 0.0009 | 0 | 0 |
| | 50 | 0.0168 | 0.0181 | 0 | 0.0008 | 0 | 0 | 0 | 0.0016 | 0 | 0 |
| | 80 | 0.0436 | 0.0477 | 0 | 0.0008 | 0 | 0 | 0 | 0.0018 | 0 | 0 |
| | 95 | 0.0676 | 0.0695 | 0 | 0.0006 | 0 | 0.0011 | 0 | 0.0018 | 0 | 0 |
| 3 | 115 | 0 | 0.0006 | 0 | 0 | 0 | 0.0008 | 0 | 0.0013 | 0.0518 | 0.0497 |
| | 125 | 0 | 0.0002 | 0 | 0.0007 | 0 | 0 | 0 | 0.0020 | 0.0689 | 0.0744 |
| | 135 | 0 | 0.0007 | 0 | 0.0007 | 0 | 0 | 0 | 0.0017 | 0.0911 | 0.0950 |
| | 155 | 0 | 0.0007 | 0 | 0.0002 | 0 | 0.0007 | 0 | 0.0007 | 0.1570 | 0.1630 |
| 4 | 20 | 0 | 0.0003 | 0 | 0 | 0.043 | 0.04 | 0 | 0.00015 | 0 | 0.0004 |
| 5 | 20 | 0 | 0.0001 | 0 | 0 | 0.07 | 0.068 | 0 | 0.0008 | 0 | 0.0002 |
| 6 | 20 | 0 | 0 | 0 | 0.0002 | 0.099 | 0.104 | 0 | 0.0007 | 0 | 0 |
| 7 | 20 | 0 | 0.0001 | 0 | 0 | 0.127 | 0.119 | 0 | 0.0011 | 0 | 0.0002 |
| 8 | 20 | 0 | 0 | 0 | 0.0007 | 0 | 0.001 | 0.052 | 0.048 | 0 | 0.0004 |
| 9 | 20 | 0 | 0 | 0 | 0.0009 | 0 | 0 | 0.115 | 0.121 | 0 | 0.0006 |
| 10 | 20 | 0 | 0.0005 | 0 | 0.0006 | 0 | 0 | 0.154 | 0.163 | 0 | 0.0004 |
| 11 | 20 | 0 | 0.0002 | 0 | 0.0006 | 0 | 0 | 0.188 | 0.195 | 0 | 0 |

EXAMPLES

Figure 4A:
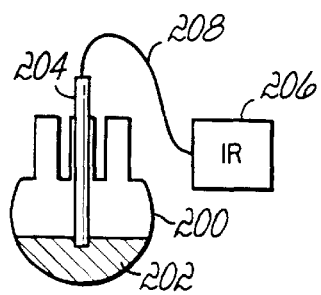
FIGS. 4A–4B are schematic representations of modes of the on-line analysis of the present invention.

In all examples pertaining to liquid analysis discussed herein, equipment as shown in FIG. 4A was used. A one liter 3-neck round bottom flask 200 was filled with 300 mL of the appropriate solution 202 and stirred at room temperature. Compositions were changed by adding the desired component via syringe directly into the flask 200 through a septum. Similarly, the flask was manually sampled by syringe in order for off-line analyses to be performed.

In terms of instrumentation, for both gas and liquid analyses an Analect Diamond 20 extended mid FTIR spectrometer 206 equipped with an Indium Arsenide (InAs) detector was used for all measurements. For liquid analyses, a one inch diameter, 0.5 mm pathlength fiber optic coupled probe 204 obtained from Axiom Analytical, Irvine, Calif. and equipped with sapphire windows was inserted directly into the one liter flask 200. This probe 204 was coupled to the spectrometer 206 via two 5 meter lengths of low OH silica fiber optic cable 208 obtained from CeramOptic Industries, East Longmeadow, Mass. A monitoring frequency of one data point per minute was maintained in all experiments unless otherwise noted.

Figure 4B:
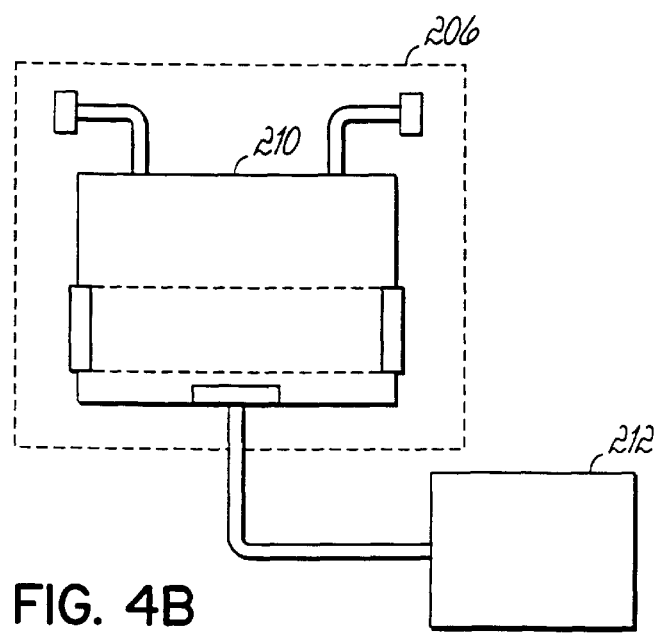

In all examples pertaining to gas analysis discussed herein, equipment as shown in FIG. 4B was used. A 100 mm pathlength, 40 mL volume, stainless steel, temperature controlled gas cell 210 obtained from Pike Technologies, Madison, Wis., and equipped with sapphire windows and valves at the inlet and outlet was placed in the sample compartment of the spectrometer 206. Liquid samples were introduced to the cell by syringing in through an open ball valve. Gases were introduced by connecting the appropriate gas cylinder equipped with a regulator, to the cell inlet valve. Compositions in the cell were changed in two ways. When the initial composition of the cell at room temperature was a liquid or a mixture of a liquid and a gas, heating the cell via a temperature controller 212 led to an increase in the vapor pressure of the liquid and hence a change in the liquid's gas phase concentration. When the initial composition of the cell was a gas, different concentrations were obtained by introducing different pressures of the gas to the cell.

In all liquid examples, the principal methods used to analyze manually obtained samples were gas chromatography (GC), Karl Fischer (KF) and weighing of residues. All of these methods are well established in vinyl acetate manufacturing with accuracies greater than or equal to +/−5%. GC analyses were carried out using a Varian Instruments, Walnut Creek, Calif. model 3400 instrument, equipped with a NUKOL® 60 meter capillary column and a flame ionization detector. Karl Fischer water analyses were carried out using an EM Sciences, Gibbstown, N.J. AQUASTAR® model VIB titrator. Polyvinyl acetate and hydroquinone were determined by heating solutions under vacuum and weighing the residue on a four figure balance.

Example 1

Figure 5:
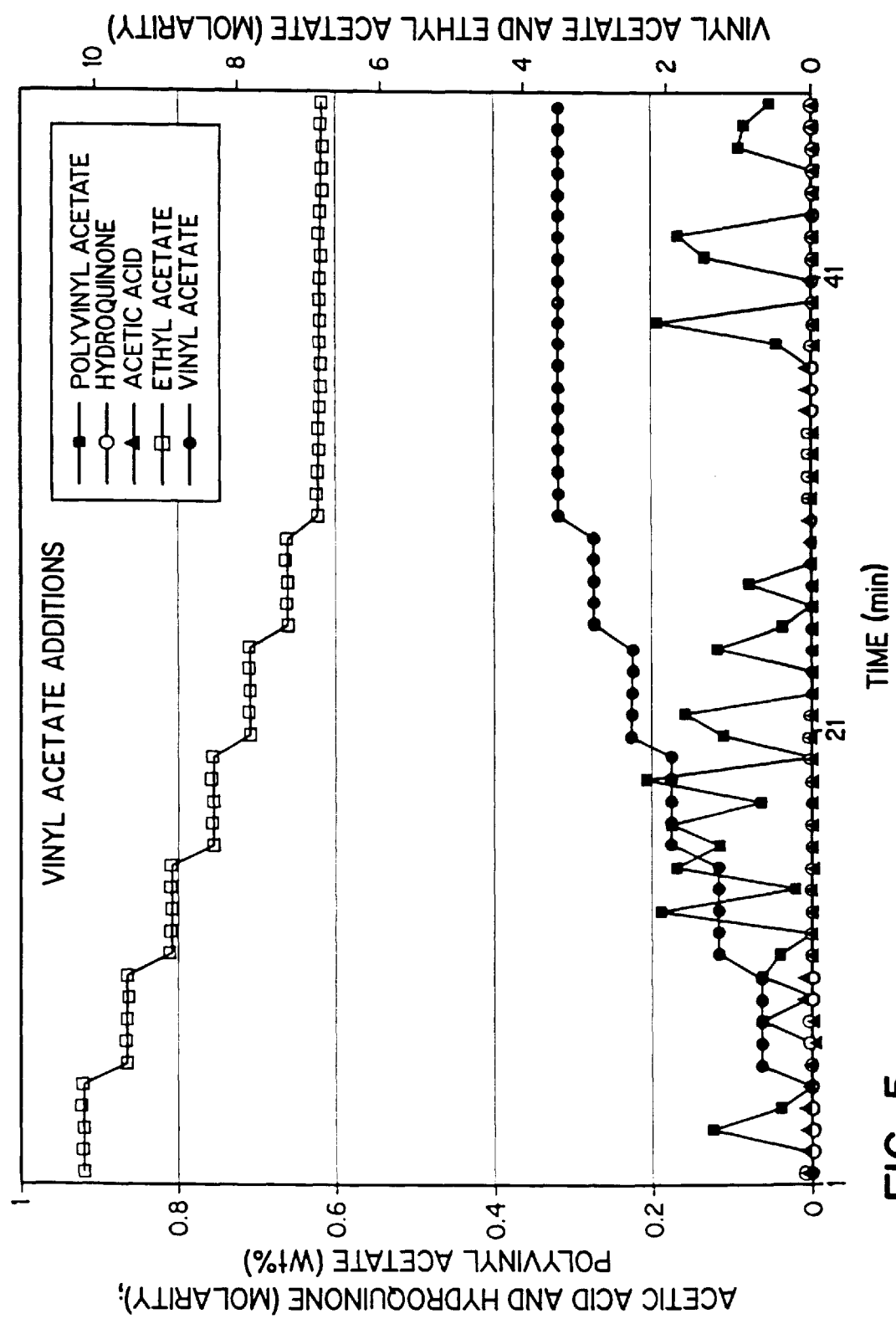
FIG. 5 is a multi-component trend file containing 50 minutes of run time data for five product tower bottoms solution components.

A product tower 140/product tower bottoms type solution 202 was stirred in the one liter flask 200 for about three hours. The initial composition of this solution 202 was essentially pure ethyl acetate as indicated in the first row of Table 11. During the first 50 minute period of monitoring, 6 aliquots of vinyl acetate were added to the flask 200 via syringe such that the composition changed from 100% ethyl acetate to about 67% ethyl acetate on a molar basis as shown in Table 11. The trend lines in FIG. 5, as determined by infrared analysis, show the incremental decreases in ethyl acetate concentration and the corresponding increases in vinyl acetate concentration associated with addition of vinyl acetate. The purpose of this first part of the experiment was to demonstrate that the ethyl acetate/vinyl acetate ratio, which can vary greatly as a function of tray level in the product tower, can be measured with great accuracy by an on-line infrared probe. This accuracy is evidenced by the excellent correlation between on-line infrared and off-line values displayed in Table 11 below. Thus, strategic placement of infrared probes on product tower trays would allow a concentration profile of the product tower 140 for its two major components to be determined. Similarly, monitoring the product tower bottoms feed 142 to the PRU 170 and the heavy waste stream 172 from the PRU 170 would allow the relative ratio of these two components to be continuously monitored. PRU operation could then be optimized to minimize vinyl acetate concentration in the heavy waste stream 172.

Figure 6:
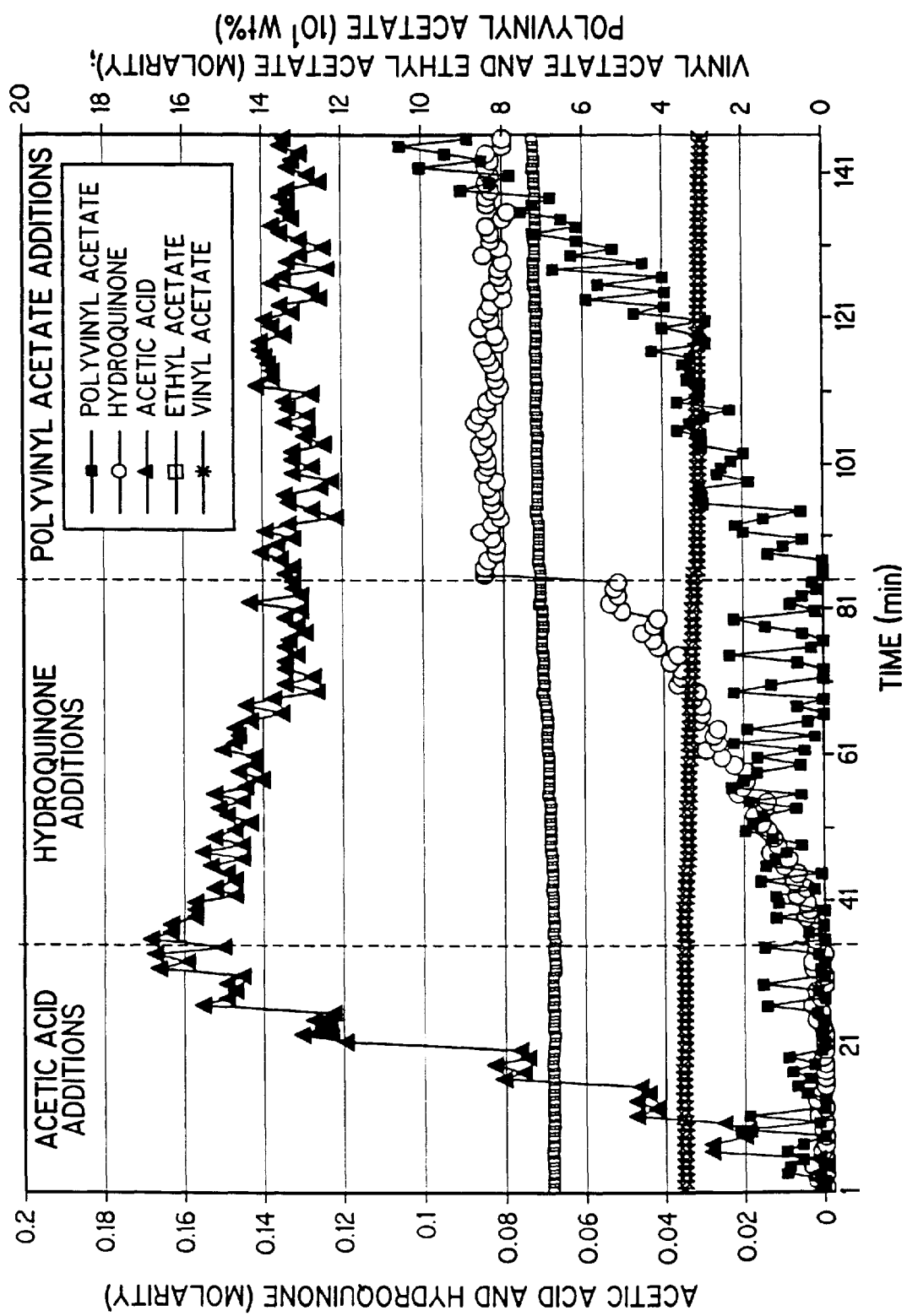
FIG. 6 is a multi-component trend file containing 150 minutes of run time data for five product tower bottoms solution components.

During the second period of this experiment totaling about 2.5 hours, aliquots of acetic acid, polymerization inhibitor (hydroquinone) and polyvinyl acetate (having an average molecular weight (weight average) of approximately 12,000) were sequentially added to the flask 200 in FIG. 4A. The first two of these components may be typically found in product tower solutions, usually at concentrations of <0.2 molar. Polyvinyl acetate is typically found in product tower solutions at concentrations of <0.5 weight percent. As polyvinyl acetate may vary in molecular weight, the concentration unit of weight percent gives a more reliable quantitation than molarity. The second block of Table 11 shows the on-line infrared and off-line GC data for the acetic acid additions, the third block shows data for hydroquinone additions and the fourth block shows data for polyvinyl acetate additions. The trend lines in FIG. 6 show the incremental increases in acetic acid, hydroquinone and polyvinyl acetate associated with the additions. As would be expected, on the basis of the lower signal to noise ratio for these lower concentration components, the data is noisier than for the higher concentration ethyl and vinyl acetate. However, much of this noise can be removed by averaging several data points. Each data point shown in Table 11 for acetic acid, hydroquinone and polyvinyl acetate is a five point average. These data indicate that an accuracy of better than +/−0.005 molar can be achieved for all concentration ranges tested for acetic acid and hydroquinone and an accuracy of better than +/−0.1 weight percent can be achieved for concentration ranges of polyvinyl acetate with a lower limit of quantitation of 0.2 weight percent.

TABLE 11

Addition of Vinyl Acetate, Acetic Acid, Hydroquinone and Polyvinyl Acetate to a Product Tower Bottoms Solution: Correlation of On-Line Extended Mid-Infrared Values with Independent Off-Line Analytical Techniques (GC/Weighing)

| Vinyl Acetate (Molar) | | Ethyl Acetate (Molar) | | Hydroquinone (Molar) | | Acetate Acid (Molar) | | Polyvinyl Acetate ($10^3$ Molar) | |
|---|---|---|---|---|---|---|---|---|---|
| Infrared | GC | Infrared | GC | Infrared | Weighing | Infrared | GC | Infrared | Weighing |
| 0.01 | 0 | 10.09 | 10.15 | 0.002 | 0 | 0.005 | 0 | 0.026 | 0 |
| 0.69 | 0.70 | 9.49 | 9.48 | 0.001 | 0 | 0.006 | 0 | 0.025 | 0 |
| 1.31 | 1.33 | 8.89 | 8.88 | 0.002 | 0 | 0.002 | 0 | 0.084 | 0 |
| 1.93 | 1.94 | 8.32 | 8.30 | 0 | 0 | 0 | 0 | 1.113 | 0 |
| 2.48 | 2.50 | 7.79 | 7.76 | 0 | 0 | 0 | 0 | 0.013 | 0 |
| 3.04 | 3.04 | 7.27 | 7.26 | 0.001 | 0 | 0.001 | 0 | 0.023 | 0 |
| 3.51 | 3.52 | 6.84 | 6.82 | 0.001 | 0 | 0.001 | 0 | 0.005 | 0 |
| 3.48 | 3.52 | 6.77 | 6.81 | 0 | 0 | 0.022 | 0.021 | 0.074 | 0 |
| 3.51 | 3.51 | 6.76 | 6.8 | 0.001 | 0 | 0.045 | 0.042 | 0.06 | 0 |
| 3.48 | 3.50 | 6.76 | 6.79 | 0 | 0 | 0.077 | 0.078 | 0.047 | 0 |
| 3.47 | 3.49 | 6.75 | 6.78 | 0.001 | 0 | 0.120 | 0.120 | 0.006 | 0 |
| 3.46 | 3.48 | 6.74 | 6.77 | 0.001 | 0 | 0.150 | 0.150 | 0.065 | 0 |
| 3.47 | 3.47 | 6.74 | 6.77 | 0.003 | 0.002 | 0.16 | 0.15 | 0.040 | 0.007 |
| 3.44 | 3.45 | 6.76 | 6.78 | 0.005 | 0.005 | 0.16 | 0.15 | 0.074 | 0 |
| 3.43 | 3.44 | 6.76 | 6.79 | 0.008 | 0.007 | 0.15 | 0.15 | 0.110 | 0.011 |
| 3.37 | 3.41 | 6.79 | 6.81 | 0.013 | 0.012 | 0.15 | 0.15 | 0.119 | 0.018 |
| 3.37 | 3.38 | 6.81 | 6.84 | 0.015 | 0.017 | 0.14 | 0.15 | 0.015 | 0.008 |
| 3.34 | 3.35 | 6.84 | 6.86 | 0.022 | 0.021 | 0.14 | 0.14 | 0.144 | 0 |
| 3.30 | 3.32 | 6.85 | 6.89 | 0.027 | 0.026 | 0.13 | 0.14 | 0.090 | 0.021 |
| 3.29 | 3.29 | 6.88 | 6.91 | 0.031 | 0.030 | 0.13 | 0.14 | 0.064 | 0 |
| 3.27 | 3.26 | 6.94 | 6.93 | 0.035 | 0.034 | 0.13 | 0.14 | 0.084 | 0.004 |
| 3.22 | 3.24 | 6.96 | 6.97 | 0.039 | 0.038 | 0.13 | 0.13 | 0.088 | 0.024 |

TABLE 11-continued

Addition of Vinyl Acetate, Acetic Acid, Hydroquinone and Polyvinyl Acetate to a Product Tower Bottoms Solution: Correlation of On-Line Extended Mid-Infrared Values with Independent Off-Line Analytical Techniques (GC/Weighing)

| Vinyl Acetate (Molar) | | Ethyl Acetate (Molar) | | Hydroquinone (Molar) | | Acetate Acid (Molar) | | Polyvinyl Acetate ($10^3$ Molar) | |
|---|---|---|---|---|---|---|---|---|---|
| Infrared | GC | Infrared | GC | Infrared | Weighing | Infrared | GC | Infrared | Weighing |
| 3.19 | 3.17 | 7.01 | 6.99 | 0.049 | 0.046 | 0.13 | 0.13 | 0.381 | 0.022 |
| 3.11 | 3.10 | 7.03 | 7.04 | 0.082 | 0.082 | 0.13 | 0.12 | 0.114 | 0.018 |
| 3.09 | 3.10 | 7.05 | 7.05 | 0.083 | 0.081 | 0.13 | 0.13 | 0.140 | 0.059 |
| 3.07 | 3.10 | 7.08 | 7.07 | 0.082 | 0.081 | 0.13 | 0.13 | 0.224 | 0.118 |
| 3.06 | 3.10 | 7.08 | 7.08 | 0.084 | 0.081 | 0.13 | 0.13 | 0.243 | 0.176 |
| 3.06 | 3.10 | 7.10 | 7.09 | 0.084 | 0.081 | 0.13 | 0.13 | 0.311 | 0.234 |
| 3.07 | 3.10 | 7.09 | 7.10 | 0.081 | 0.081 | 0.13 | 0.13 | 0.322 | 0.292 |
| 3.05 | 3.10 | 7.09 | 7.11 | 0.082 | 0.081 | 0.13 | 0.13 | 0.345 | 0.350 |
| 3.04 | 3.00 | 7.11 | 7.10 | 0.082 | 0.080 | 0.13 | 0.13 | 0.476 | 0.427 |
| 3.03 | 3.00 | 7.13 | 7.12 | 0.080 | 0.080 | 0.13 | 0.13 | 0.529 | 0.503 |
| 3.02 | 3.00 | 7.12 | 7.12 | 0.082 | 0.080 | 0.13 | 0.13 | 0.680 | 0.653 |
| 3.02 | 3.00 | 7.12 | 7.13 | 0.081 | 0.079 | 0.13 | 0.13 | 0.833 | 0.800 |
| 3.01 | 3.00 | 7.15 | 7.15 | 0.080 | 0.078 | 0.13 | 0.13 | 0.954 | 1.020 |

Example 2

Figure 7:
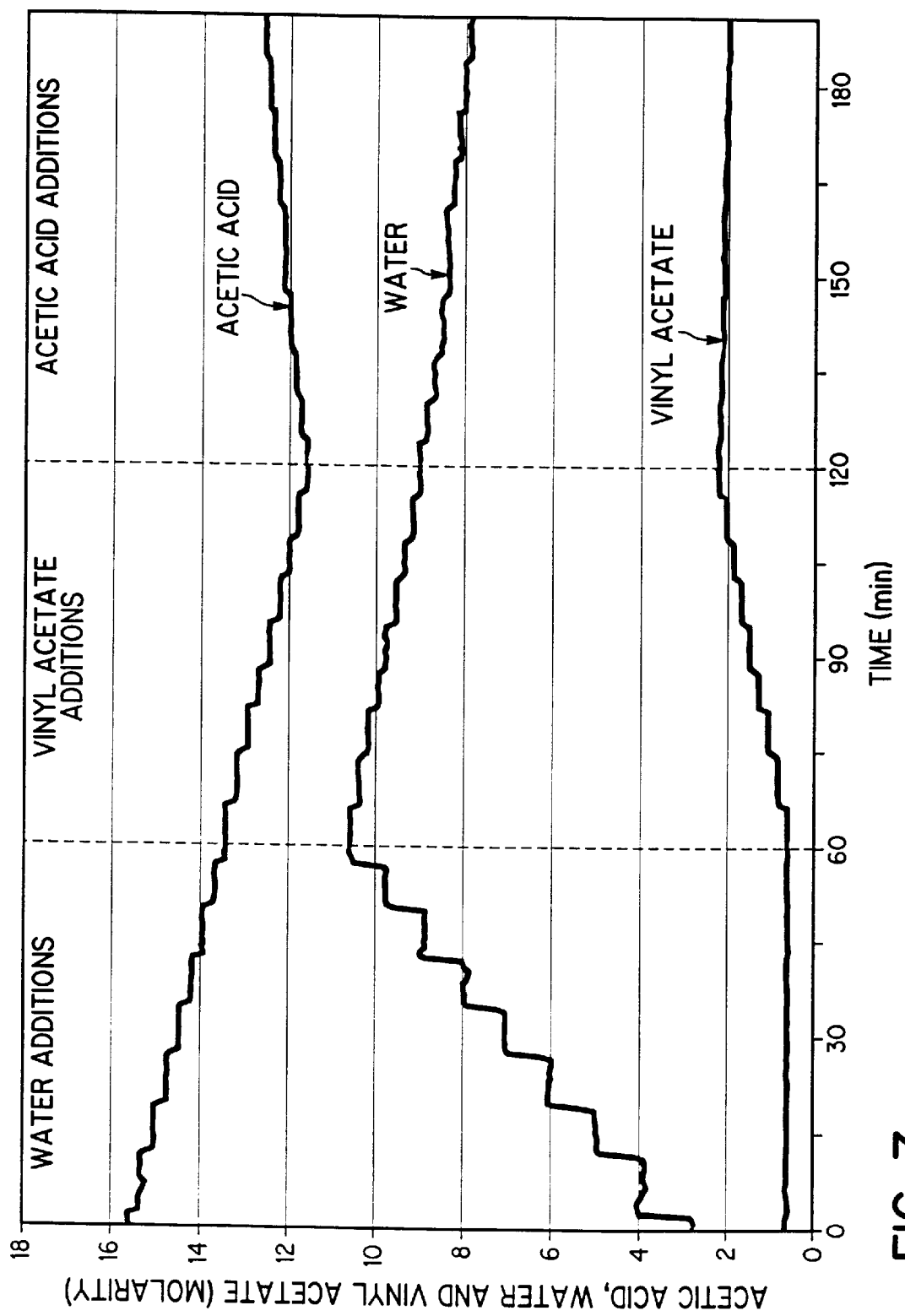
FIG. 7 is a multi-component trend file containing 180 minutes of run time data for three absorber bottoms solution components.

An absorber 30 bottoms type solution 202 was stirred in the one liter flask 200 for about three hours. A monitoring frequency of one data point per 30 seconds was used. The solution 202 of starting composition as shown in the first row of Table 12 was used. Several aliquots of water, vinyl acetate and acetic acid were sequentially added to the flask 200 via syringe such that the concentrations of all three components varied over a wide range. The trend lines shown in FIG. 7 show the incremental changes in each of the three components associated with these additions. The purpose of this experiment was to demonstrate that the molar concentrations of acetic acid, vinyl acetate and water in a varying mixture can all be measured accurately by on-line infrared. Results in Table 12 show the correlation between off-line analyses of manual samples with corresponding on-line infrared values. All components can be measured using the on-line infrared equipment with a correlation of +/−0.1 molar or better relative to off-line analysis. A similar analysis would apply to the scrubber 40 bottoms with the exception that little or no vinyl acetate would be present. Thus, on-line analysis of both absorber 30 and scrubber 40 bottoms would provide information to allow optimization of the primary tower.

TABLE 12

Addition of Water, Vinyl Acetate and Acetic Acid to an Absorber Bottoms Solution: Correlation of On-Line Extended Mid-Infrared Values with Independent Off-Line Analytical Techniques (Karl Fischer/GC)

| Water (Molar) | | Vinyl Acetate (Molar) | | Acetic Acid (Molar) | |
|---|---|---|---|---|---|
| Infrared | Karl Fischer | Infrared | GC | Infrared | GC |
| 2.80 | 2.85 | 0.68 | 0.66 | 15.43 | 15.54 |
| 4.13 | 3.91 | 0.64 | 0.65 | 15.08 | 15.22 |
| 5.01 | 4.94 | 0.64 | 0.64 | 14.85 | 14.91 |
| 5.97 | 5.92 | 0.63 | 0.62 | 14.56 | 14.63 |
| 6.99 | 6.87 | 0.63 | 0.62 | 14.27 | 14.35 |
| 7.93 | 7.78 | 0.61 | 0.60 | 14.02 | 14.07 |
| 8.78 | 8.66 | 0.60 | 0.59 | 13.75 | 13.83 |
| 9.65 | 9.50 | 0.59 | 0.58 | 13.49 | 13.58 |
| 10.42 | 10.32 | 0.57 | 0.57 | 13.25 | 13.33 |
| 10.11 | 10.25 | 0.79 | 0.78 | 12.97 | 13.06 |
| 9.91 | 10.01 | 0.97 | 0.98 | 12.74 | 12.82 |
| 9.72 | 9.76 | 1.18 | 1.17 | 12.47 | 12.55 |
| 9.54 | 9.61 | 1.38 | 1.36 | 12.21 | 12.32 |
| 9.35 | 9.41 | 1.55 | 1.54 | 11.97 | 12.08 |
| 9.18 | 9.21 | 1.71 | 1.71 | 11.77 | 11.86 |
| 9.02 | 9.02 | 1.88 | 1.87 | 11.56 | 11.62 |
| 8.85 | 8.86 | 2.04 | 2.03 | 11.35 | 11.44 |
| 8.69 | 8.67 | 2.01 | 1.99 | 11.50 | 11.55 |
| 8.48 | 8.50 | 1.97 | 1.95 | 11.64 | 11.67 |
| 8.35 | 8.33 | 1.90 | 1.91 | 11.74 | 11.79 |
| 8.16 | 8.18 | 1.86 | 1.88 | 11.89 | 11.90 |
| 8.04 | 8.02 | 1.84 | 1.84 | 11.96 | 12.01 |
| 7.92 | 7.88 | 1.82 | 1.81 | 12.05 | 12.12 |
| 7.79 | 7.73 | 1.79 | 1.79 | 12.15 | 12.22 |
| 7.63 | 7.59 | 1.75 | 1.75 | 12.25 | 12.32 |

Example 3

Figure 8:
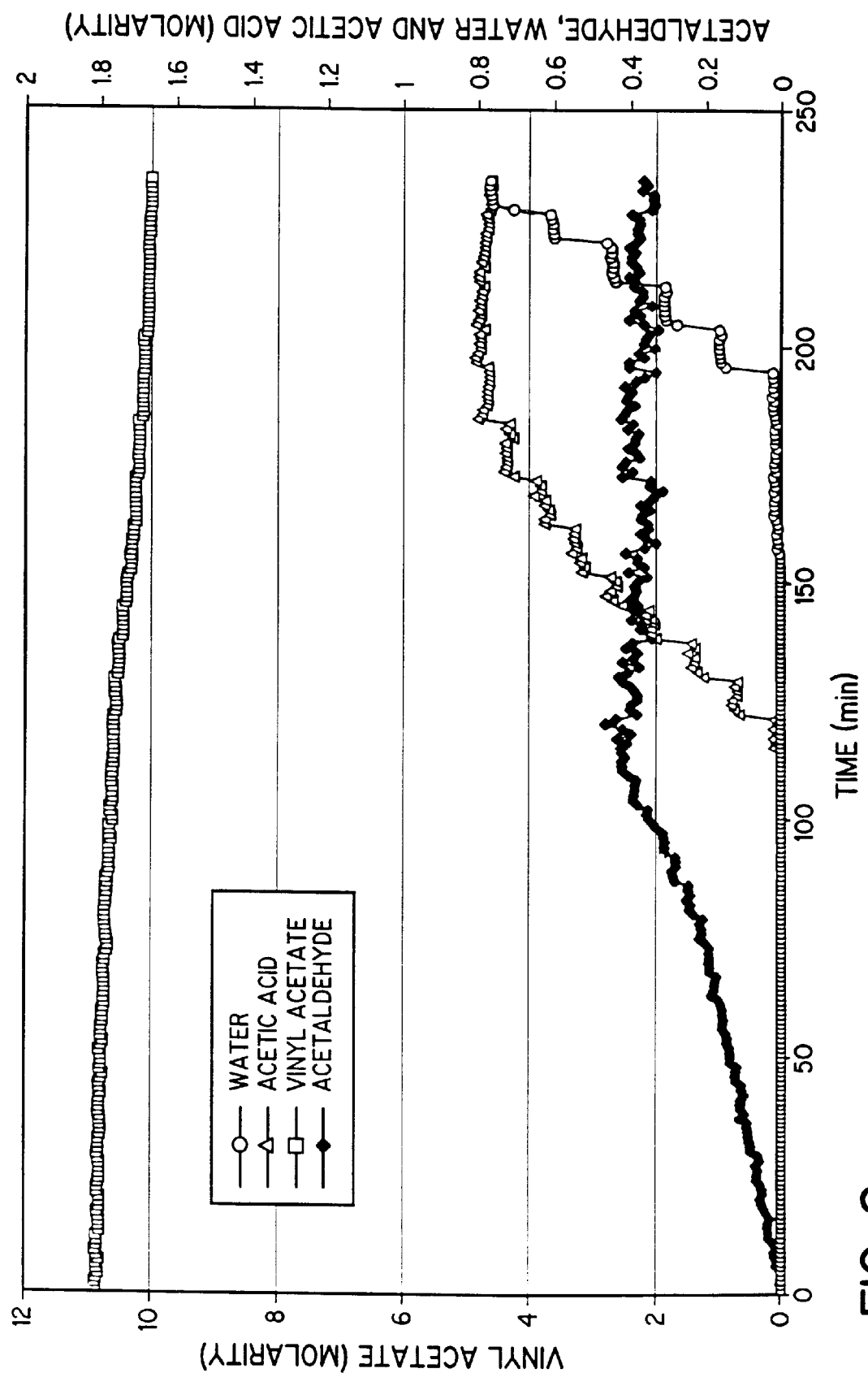
FIG. 8 is a multi-component trend file containing 240 minutes of run time data for four light phase decanter solution components.

A decanter 100 light phase type solution 202 was stirred in the one liter flask 200 for about four hours with a monitoring frequency of one data point per minute. The starting solution 202 was pure vinyl acetate as indicated in the first row of Table 13. To mimic conditions that might exist in a process decanter 100 light phase, several aliquots of acetaldehyde, acetic acid and water were sequentially added to the flask 200 via syringe such that their concentrations varied from zero to a maximum of about 0.8 molar. The trend lines in FIG. 8 show the incremental increases in each of the component concentrations associated with the additions. The purpose of this experiment was to demonstrate that relatively small changes in acetic acid and water can be detected and quantified. As phase separation can be compromised by sufficiently high concentrations of acetic acid in the decanter 100, continuous updates of decanter component concentrations by on-line infrared measurement may be used to monitor decanter performance and permit subsequent optimization.

TABLE 13

Addition of Acetaldehyde, Acetic Acid and Water to a Decanter Light Phase Solution: Correlation of On-Line Extended Mid-Infrared Values with Independent Off-Line Analytical Technique (GC)

| Vinyl Acetate (Molar) | | Acetaldehyde (Molar) | | Water (Molar) | | Acetic Acid (Molar) | |
|---|---|---|---|---|---|---|---|
| Infrared | GC | Infrared | GC | Infrared | GC | Infrared | GC |
| 10.88 | 10.78 | 0.006 | 0 | 0 | 0 | 0.002 | 0 |
| 10.88 | 10.79 | 0.018 | 0.018 | 0 | 0 | 0 | 0 |
| 10.86 | 10.72 | 0.036 | 0.037 | 0 | 0 | 0 | 0 |
| 10.85 | 10.72 | 0.054 | 0.055 | 0 | 0 | 0 | 0 |
| 10.84 | 10.75 | 0.068 | 0.073 | 0 | 0 | 0 | 0.011 |
| 10.84 | 10.70 | 0.091 | 0.092 | 0 | 0 | 0.004 | 0.008 |
| 10.84 | 10.73 | 0.111 | 0.109 | 0 | 0 | 0.007 | 0 |
| 10.82 | 10.71 | 0.138 | 0.129 | 0 | 0 | 0.003 | 0 |
| 10.82 | 10.72 | 0.159 | 0.146 | 0 | 0 | 0 | 0 |
| 10.77 | 10.69 | 0.179 | 0.165 | 0 | 0 | 0 | 0 |
| 10.76 | 10.70 | 0.200 | 0.200 | 0 | 0 | 0.007 | 0.004 |
| 10.75 | 10.70 | 0.224 | 0.218 | 0 | 0 | 0.007 | 0.006 |
| 10.73 | 10.69 | 0.259 | 0.255 | 0 | 0 | 0.004 | 0 |
| 10.71 | 10.65 | 2.940 | 0.292 | 0 | 0 | 0 | 0 |
| 10.72 | 10.67 | 0.320 | 0.327 | 0 | 0 | 0 | 0 |
| 10.66 | 10.62 | 0.373 | 0.362 | 0 | 0 | 0 | 0 |
| 10.63 | 10.61 | 0.428 | 0.407 | 0 | 0 | 0 | 0 |
| 10.59 | 10.51 | 0.402 | 0.390 | 0 | 0 | 0.127 | 0.131 |
| 10.55 | 10.47 | 0.411 | 0.386 | 0 | 0 | 0.235 | 0.230 |
| 10.47 | 10.42 | 0.386 | 0.380 | 0 | 0 | 0.351 | 0.355 |
| 10.41 | 10.44 | 0.389 | 0.375 | 0 | 0 | 0.455 | 0.449 |
| 10.35 | 10.37 | 0.364 | 0.376 | 0.004 | 0 | 0.542 | 0.552 |
| 10.27 | 10.32 | 0.358 | 0.371 | 0.011 | 0 | 0.639 | 0.636 |
| 10.22 | 10.26 | 0.387 | 0.367 | 0.009 | 0 | 0.731 | 0.730 |
| 10.16 | 10.18 | 0.384 | 0.369 | 0.013 | 0 | 0.795 | 0.802 |
| 10.14 | 10.08 | 0.364 | 0.359 | 0.164 | 0.169 | 0.794 | 0.800 |
| 10.07 | 10.01 | 0.379 | 0.351 | 0.311 | 0.307 | 0.792 | 0.800 |
| 10.05 | 10.07 | 0.391 | 0.355 | 0.449 | 0.444 | 0.790 | 0.788 |
| 10.05 | 10.07 | 0.381 | 0.353 | 0.602 | 0.597 | 0.781 | 0.785 |
| 10.02 | 10.09 | 0.355 | 0.351 | 0.769 | 0.760 | 0.774 | 0.781 |

Example 4

Figure 9:
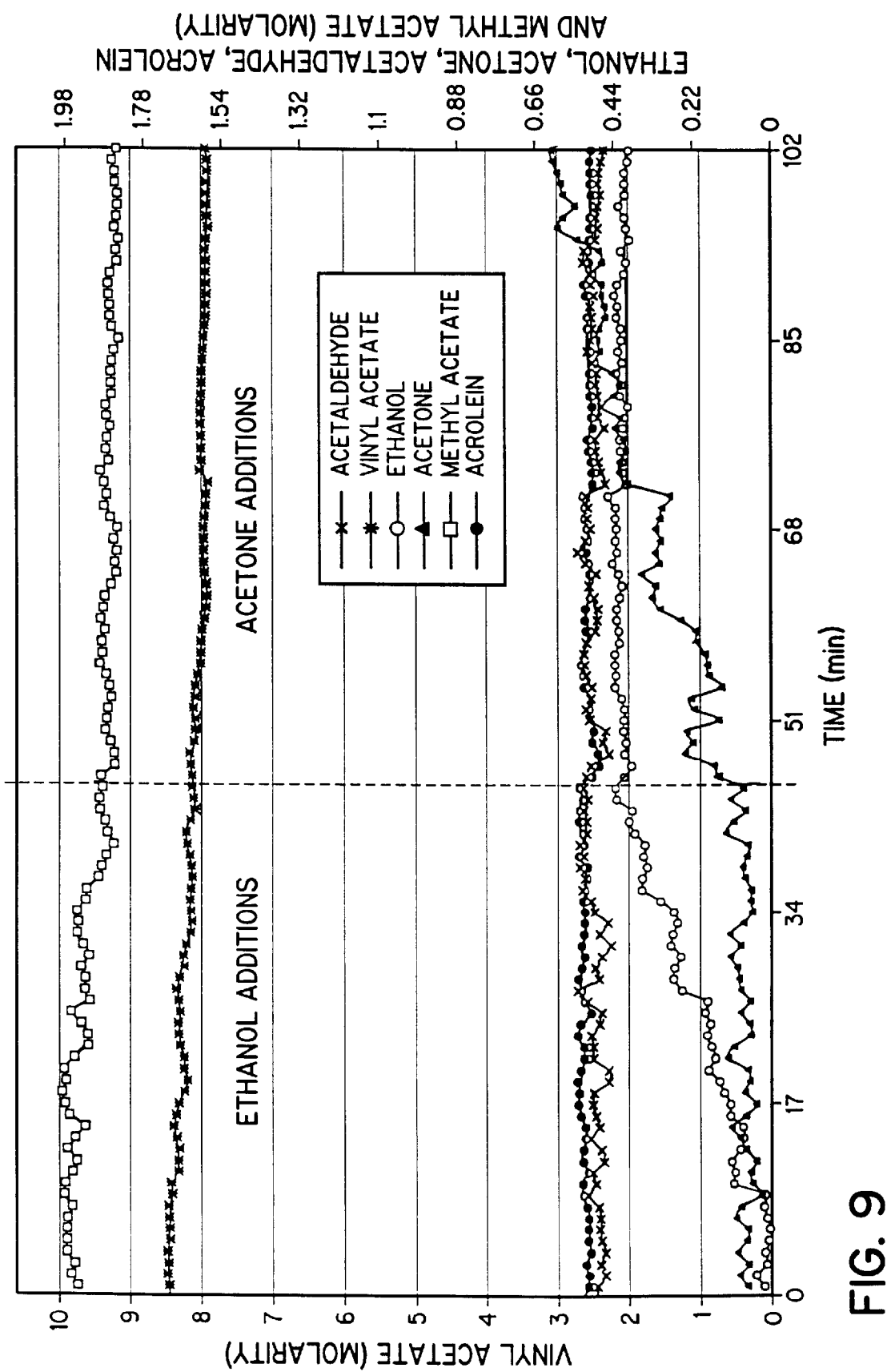
FIG. 9 is a multi-component trend file containing the first 100 minutes of run time data for six lights tower reflux drum solution components.
Figure 10:
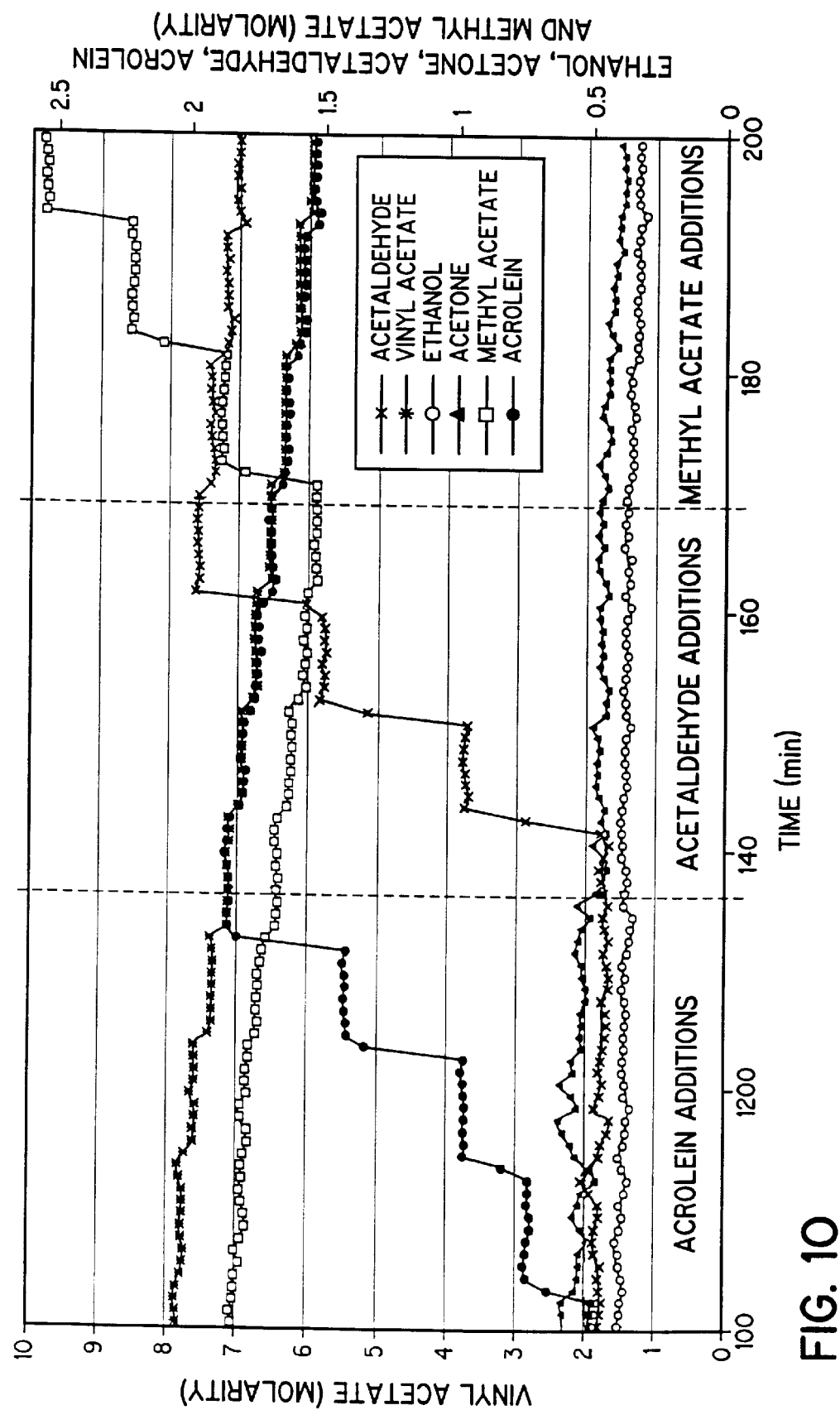
FIG. 10 is a multi-component trend file containing the second 100 minutes of run time data for six lights tower reflux drum solution components.

A lights tower reflux drum 133 type solution was stirred in the one liter flask 200 for about three hours with a monitoring frequency of one data point per minute. The composition of the starting solution 202 is shown in the first row of Table 14. During the first 100 minute period of monitoring, several aliquots of ethanol and acetone were sequentially added to the flask 200 via syringe such that their concentrations ranged from 0.0 to 0.6 molar. The incremental increases in ethanol and acetone concentration during this first 100 minute period are shown in FIG. 9 and the correlation between on-line and off-line measurements is shown in the first two blocks of Table 14. During a second 100 minute period, several aliquots of acrolein, acetaldehyde and methyl acetate were sequentially added to the flask 200. The trend lines associated with these additions during the second 100 minute period are shown in FIG. 10 and the correlation between on-line and off-line measurements is contained in the third, fourth and fifth blocks of Table 14. The purpose of this experiment was to demonstrate that all six solution components that may be expected to be present in the lights tower reflux drum 133 at appreciable concentration can be detected and quantified. The correlation data in Table 14 show excellent accuracy in measurement of all components by on-line infrared analysis as evidenced by the close correlation to off-line measurements. Thus, measurement of all of these components under process conditions would be diagnostic of lights tower 130 performance and could be used to tune lights tower performance to minimize loss of vinyl acetate in lights tower overhead 131 while keeping these impurities out of the bottom product 132.

TABLE 14

Addition of Ethanol, Acetone, Acrolein, Actaldehyde and Methyl Acetate to a Purification Lights Tower Reflux Solution: Correlation of On-Line Extended Mid-Infrared Values with Independent Off-Line Analytical Technique (GC)

| Ethanol (Molar) | | Acetone (Molar) | | Acrolein (Molar) | | Acetaldehyde (Molar) | | Methyl Acetate (Molar) | | Vinyl Acetate (Molar) | |
|---|---|---|---|---|---|---|---|---|---|---|---|
| Infrared | GC | Infrared | GC | Infrared | GC | Infrared | GC | Infrared | GC | Infrared | GC |
| 0.019 | 0 | 0.084 | 0.106 | 0.519 | 0.534 | 0.482 | 0.510 | 1.97 | 1.94 | 8.46 | 8.40 |
| 0.102 | 0.086 | 0.102 | 0.104 | 0.534 | 0.531 | 0.494 | 0.508 | 1.94 | 1.93 | 8.35 | 8.35 |
| 0.169 | 0.175 | 0.081 | 0.104 | 0.534 | 0.528 | 0.489 | 0.508 | 1.91 | 1.92 | 8.29 | 8.33 |
| 0.269 | 0.254 | 0.081 | 0.103 | 0.530 | 0.527 | 0.470 | 0.502 | 1.91 | 1.92 | 8.17 | 8.30 |

TABLE 14-continued

Addition of Ethanol, Acetone, Acrolein, Actaldehyde and Methyl Acetate to a Purification Lights Tower Reflux Solution: Correlation of On-Line Extended Mid-Infrared Values with Independent Off-Line Analytical Technique (GC)

| Ethanol (Molar) | | Acetone (Molar) | | Acrolein (Molar) | | Acetaldehyde (Molar) | | Methyl Acetate (Molar) | | Vinyl Acetate (Molar) | |
|---|---|---|---|---|---|---|---|---|---|---|---|
| Infrared | GC | Infrared | GC | Infrared | GC | Infrared | GC | Infrared | GC | Infrared | GC |
| 0.357 | 0.340 | 0.100 | 0.102 | 0.525 | 0.523 | 0.525 | 0.500 | 1.87 | 1.90 | 8.13 | 8.23 |
| 0.405 | 0.433 | 0.092 | 0.103 | 0.517 | 0.521 | 0.513 | 0.494 | 1.85 | 1.90 | 8.09 | 8.19 |
| 0.416 | 0.430 | 0.193 | 0.200 | 0.515 | 0.516 | 0.506 | 0.493 | 1.85 | 1.87 | 7.98 | 8.13 |
| 0.423 | 0.427 | 0.315 | 0.295 | 0.511 | 0.513 | 0.510 | 0.490 | 1.83 | 1.86 | 7.92 | 8.08 |
| 0.417 | 0.422 | 0.414 | 0.388 | 0.484 | 0.509 | 0.492 | 0.489 | 1.84 | 1.84 | 7.92 | 8.05 |
| 0.414 | 0.421 | 0.472 | 0.481 | 0.504 | 0.508 | 0.497 | 0.483 | 1.83 | 1.82 | 7.91 | 7.96 |
| 0.404 | 0.417 | 0.586 | 0.574 | 0.497 | 0.502 | 0.474 | 0.480 | 1.82 | 1.82 | 7.88 | 7.94 |
| 0.391 | 0.411 | 0.548 | 0.565 | 0.736 | 0.737 | 0.485 | 0.475 | 1.79 | 1.80 | 7.80 | 7.78 |
| 0.381 | 0.404 | 0.578 | 0.557 | 0.971 | 0.976 | 0.466 | 0.464 | 1.77 | 1.77 | 7.64 | 7.65 |
| 0.380 | 0.392 | 0.537 | 0.536 | 1.411 | 1.401 | 0.451 | 0.451 | 1.72 | 1.67 | 7.37 | 7.44 |
| 0.376 | 0.379 | 0.502 | 0.523 | 1.861 | 1.843 | 0.459 | 0.435 | 1.66 | 1.59 | 7.14 | 7.16 |
| 0.379 | 0.368 | 0.481 | 0.505 | 1.805 | 1.786 | 0.970 | 0.976 | 1.61 | 1.55 | 6.95 | 6.95 |
| 0.375 | 0.356 | 0.465 | 0.489 | 1.742 | 1.731 | 1.503 | 1.477 | 1.56 | 1.55 | 6.75 | 6.74 |
| 0.366 | 0.345 | 0.470 | 0.476 | 1.695 | 1.679 | 1.976 | 1.992 | 1.52 | 1.48 | 6.54 | 6.53 |
| 0.356 | 0.335 | 0.456 | 0.460 | 1.635 | 1.627 | 1.922 | 1.934 | 1.88 | 1.85 | 6.32 | 6.33 |
| 0.332 | 0.324 | 0.422 | 0.445 | 1.568 | 1.576 | 1.858 | 1.866 | 2.22 | 2.16 | 6.12 | 6.14 |
| 0.324 | 0.314 | 0.392 | 0.431 | 1.530 | 1.527 | 1.820 | 1.808 | 2.54 | 2.51 | 5.93 | 5.95 |

Example 5

Figure 11:
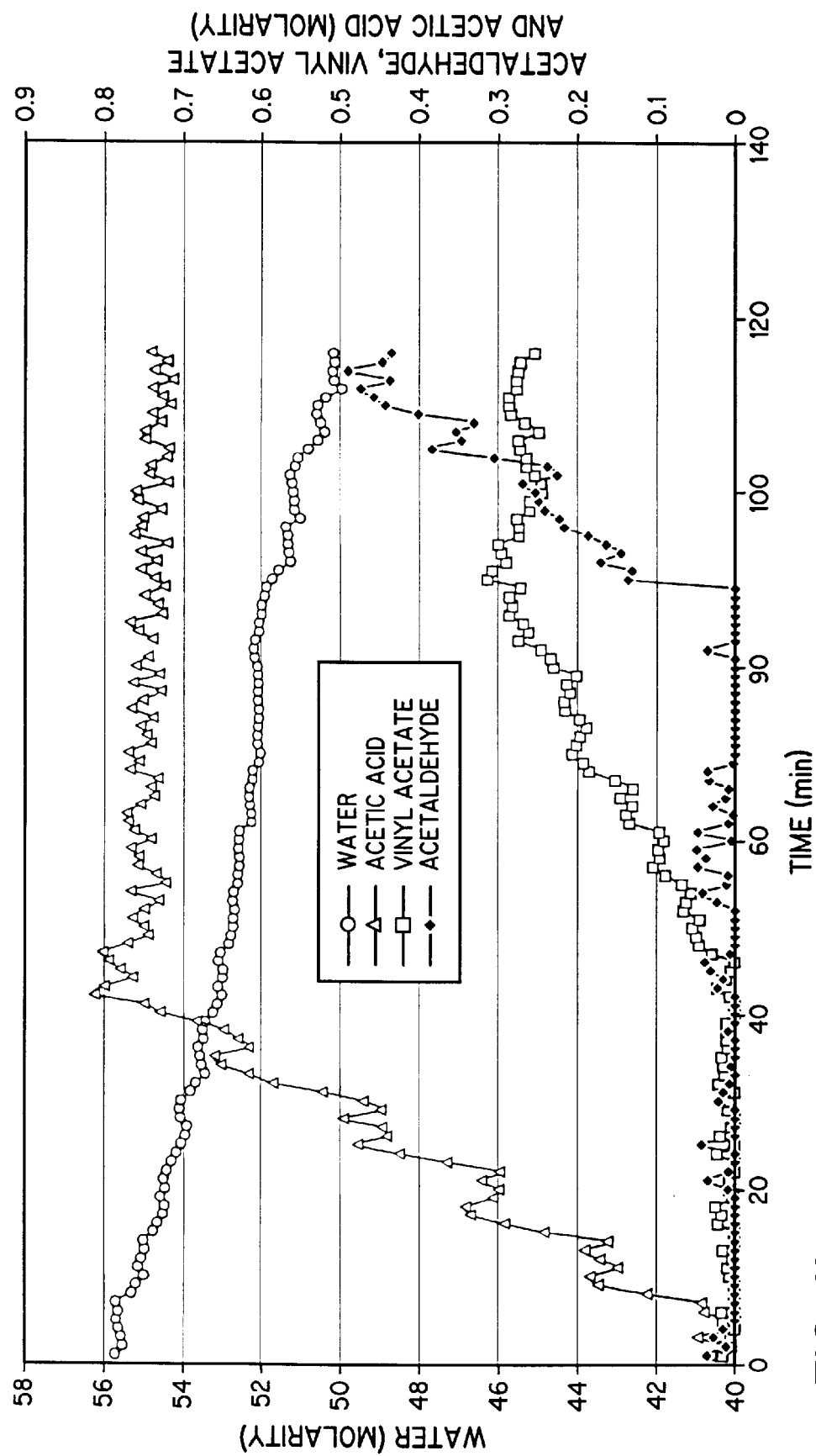
FIG. 11 is a multi-component trend file containing 116 minutes of run time data for four heavy phase decanter solution components.

A decanter 100 heavy phase type solution 202 was stirred in the one liter flask for about 2 hours with a monitoring frequency of one data point per minute. The starting solution was pure water as indicated in the first row of Table 15. To mimic conditions that might exist in a process decanter heavy phase, several aliquots of acetic acid, vinyl acetate and acetaldehyde were sequentially added to the flask via syringe such that their concentrations varied from zero to a maximum of about 0.8 molar. The trend lines in FIG. 11 show the incremental increases in each of the component concentrations associated with the additions. The purpose of this experiment was to demonstrate that relatively small changes in acetic acid and water concentrations can be detected and quantified in the decanter 100 heavy phase and that quantification of these two components is not impacted by variable concentrations of acetaldehyde or vinyl acetate in the heavy phase. Results in Table 15 show the correlation between off-line analyses of manual samples with corresponding on-line infrared values. This table shows that at the very high concentrations of water present in the decanter 100 heavy phase, water can be measured with an accuracy of +/−0.2 molar or better. Similarly, acetic acid, which may be present at low concentration in the decanter 100 heavy phase, can be measured with an accuracy of +/−0.03 molar or better. Quantitative analysis of the decanter 100 heavy phase would thus complement the similar analysis of decanter 100 light phase as described in Example 3. This total analysis of decanter 100 solution would allow prompt detection of compositional changes that might eventually impact phase separation.

TABLE 15

Addition of Acetic Acid, Vinyl Acetate and Water to Decanter Heavy Phase Type Solution: Correlation of On-Line Extended Mid-Infrared Values with Independent Off-Line Analyses (Karl Fischer/GC)

| Water (Molar) | | Acetic Acid (Molar) | | Vinyl Acetate (Molar) | | Acetaldehyde (Molar) | |
|---|---|---|---|---|---|---|---|
| Infrared | Karl Fischer | Infrared | GC | Infrared | GC | Infrared | GC |
| 55.66 | 55.49 | 0.034 | 0 | 0.007 | 0.001 | 0.020 | 0 |
| 55.17 | 55.06 | 0.174 | 0.158 | 0.005 | 0 | 0 | 0 |
| 54.43 | 54.57 | 0.298 | 0.314 | 0.021 | 0 | 0 | 0 |
| 54.14 | 54.01 | 0.449 | 0.467 | 0.011 | 0 | 0.007 | 0.001 |
| 53.39 | 53.54 | 0.649 | 0.622 | 0.006 | 0.002 | 0.004 | 0.002 |
| 52.98 | 53.07 | 0.800 | 0.771 | 0.002 | 0 | 0.009 | 0 |
| 52.72 | 52.84 | 0.779 | 0.767 | 0.039 | 0.048 | 0.016 | 0 |
| 52.58 | 52.61 | 0.758 | 0.763 | 0.105 | 0.096 | 0.029 | 0 |
| 52.27 | 52.38 | 0.764 | 0.759 | 0.130 | 0.144 | 0.027 | 0 |
| 52.06 | 52.15 | 0.750 | 0.755 | 0.202 | 0.190 | 0 | 0 |
| 52.02 | 51.92 | 0.755 | 0.752 | 0.245 | 0.236 | 0.006 | 0 |
| 51.87 | 51.70 | 0.750 | 0.746 | 0.281 | 0.281 | 0.001 | 0 |
| 51.36 | 51.32 | 0.747 | 0.738 | 0.285 | 0.277 | 0.136 | 0.124 |
| 51.12 | 50.96 | 0.747 | 0.743 | 0.264 | 0.279 | 0.223 | 0.247 |
| 50.55 | 50.60 | 0.738 | 0.732 | 0.274 | 0.275 | 0.346 | 0.368 |
| 50.16 | 50.25 | 0.734 | 0.727 | 0.276 | 0.275 | 0.459 | 0.489 |

Example 6

Figure 12:
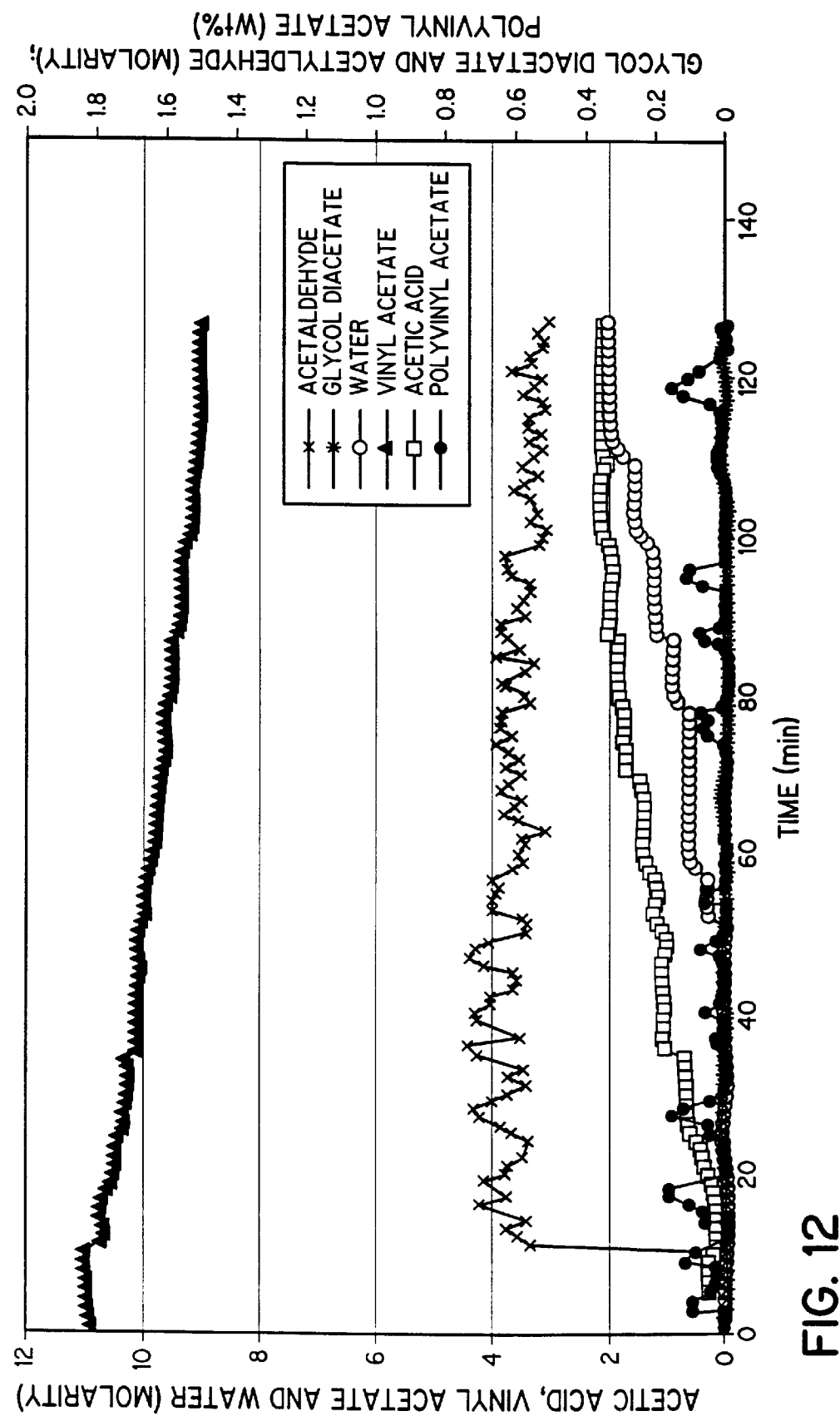
FIG. 12 is a multi-component trend file containing 127 minutes of run time data for six product tower top solution components.
Figure 13:
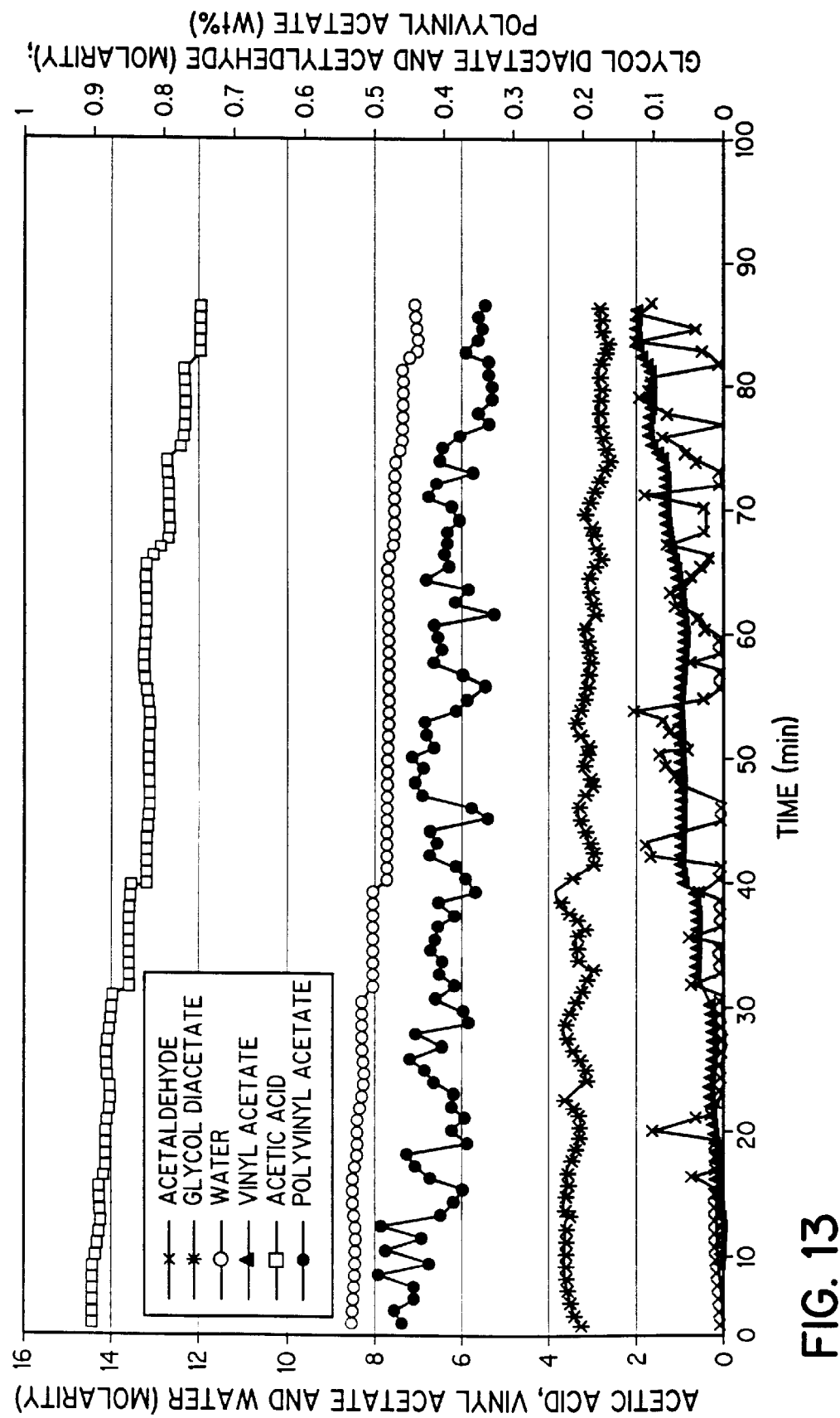
FIG. 13 is a multi-component trend file containing 86 minutes of run time data for six primary tower bottoms solution components.

A solution 202 representative of the top portion of the primary tower 90 was stirred in the one liter flask for about 2 hours with a monitoring frequency of one data point per minute. The starting solution was pure vinyl acetate as shown in the first row of Table 16. An aliquot of acetaldehyde was then added to the flask such that the acetaldehyde concentration was about 0.6 molar. As shown in Table 16, acetaldehyde can be measured with an accuracy of +/−0.05 molar or better in the 0 to 0.6 molar range. Three aliquots of acetic acid were then added to the flask followed by several aliquots of acetic acid/water mixtures such that the concentrations of water and acetic acid were varied from zero to a maximum of about 2 molar. The trend lines in FIG. 12 show the incremental increases in the component concentrations associated with the additions and the corresponding decrease in vinyl acetate concentration. Table 16 and FIG. 12 show that the four components that might be expected to be present at or towards the top of the primary tower 90 can all be measured with a high degree of accuracy ranging from about +/−0.2 molar for vinyl acetate to about +/−0.05 molar for acetaldehyde. The plot and table also contain data for polyvinyl acetate and glycol diacetate, high boiling components that would not be expected at the top of the primary tower 90. Neither of these two components was added but the calibration models were used to indicate if any false positive readings would result in response to changing concentrations of the four components likely to be present. As Table 16 and FIG. 12 show, the variability around zero is about 0.01 molar for glycol diacetate and about 0.08 wt. % for polyvinyl acetate.

water, glycol diacetate and polyvinyl acetate as shown in the first row of Table 17. This starting solution represents the maximum concentrations of water, glycol diacetate and polyvinyl acetate that might be expected in the primary tower 90 bottoms. Several aliquots of vinyl acetate were then added to the flask such that the concentration varied from zero to about 2 molar. This range encompasses the minimum and maximum concentration of vinyl acetate that would be anticipated to be present. The trend lines in FIG. 13 show the incremental increases in vinyl acetate associated with the additions. The corresponding decreases in other components due to dilution can also be seen in FIG. 13 and in Table 17. As a significant portion of the primary tower bottoms solution is used to recycle acetic acid to the reaction section via stream 94, it is important to have an accurate knowledge of the acetic acid/water ratio of the bottoms solution. The data in Table 17 show that an accuracy of +/−0.1 molar or better can be achieved for both water and acetic acid. Similar or better accuracy can also be achieved for the minor components that may be present in the bottom solution. The combination of data obtainable from the analyses in Example 6 for the top of the primary tower 90 and in this example for the primary tower bottoms would allow close control of primary tower operation to be achieved. For example, the primary tower bottoms temperature could be controlled to maintain the desired acetic acid/water ratio based on the on-line infrared analysis. The ability to effectively quantitatively analyze primary tower 90 top and bottom solutions which represent the two extremes of component concentrations also means that intermediate positions with intermediate solution compositions (and rela-

TABLE 16

Addition of Acetic Acid, Vinyl Acetate and Water to Primary Tower Top Type Solution: Correlation of Extended Mid-Infrared Values with Independent Off-Line Analyses (GC/Karl Fischer/Weighing)

| Vinyl Acetate (Molar) | | Acetic Acid (Molar) | | Water (Molar) | | Acetaldehyde (Molar) | | Glycol Diacetate (Molar) | | Polyvinyl Acetate (Wt %) | |
| --- | --- | --- | --- | --- | --- | --- | --- | --- | --- | --- | --- |
| Infrared | GC | Infrared | GC | Infrared | Karl Fischer | Infrared | GC | Infrared | GC | Infrared | Weighing |
| 10.90 | 10.86 | 0.00 | 0.00 | 0.02 | 0.00 | 0.05 | 0.01 | 0.005 | 0 | 0.050 | 0 |
| 10.66 | 10.43 | 0.02 | 0.00 | 0.06 | 0.01 | 0.64 | 0.70 | 0.002 | 0.001 | 0.020 | 0 |
| 10.42 | 10.24 | 0.32 | 0.31 | 0.05 | 0.00 | 0.61 | 0.68 | 0.006 | 0 | 0.004 | 0 |
| 10.22 | 10.06 | 0.59 | 0.62 | 0.06 | 0.00 | 0.63 | 0.67 | 0.003 | 0 | 0.070 | 0.01 |
| 10.08 | 9.88 | 0.96 | 0.93 | 0.04 | 0.00 | 0.64 | 0.66 | 0.002 | 0.001 | 0.020 | 0.01 |
| 9.88 | 9.74 | 1.10 | 1.07 | 0.29 | 0.26 | 0.65 | 0.65 | 0.001 | 0 | 0.004 | 0.01 |
| 9.72 | 9.60 | 1.32 | 1.21 | 0.52 | 0.51 | 0.59 | 0.64 | 0.007 | 0 | 0.001 | 0 |
| 9.59 | 9.43 | 1.64 | 1.50 | 0.60 | 0.56 | 0.60 | 0.64 | 0 | 0 | 0.030 | 0 |
| 9.41 | 9.29 | 1.77 | 1.64 | 0.79 | 0.75 | 0.58 | 0.62 | 0 | 0 | 0.020 | 0 |
| 9.26 | 9.15 | 1.93 | 1.78 | 1.01 | 1.00 | 0.57 | 0.61 | 0 | 0.002 | 0.040 | 0.01 |
| 9.12 | 9.02 | 2.04 | 1.91 | 1.29 | 1.25 | 0.57 | 0.60 | 0.002 | 0 | 0.002 | 0.01 |
| 8.96 | 8.89 | 2.09 | 1.97 | 1.82 | 1.71 | 0.54 | 0.59 | 0.011 | 0 | 0.080 | 0 |
| 8.96 | 8.88 | 2.07 | 1.97 | 1.80 | 1.71 | 0.53 | 0.59 | 0.010 | 0 | 0.030 | 0 |

Example 7

A solution 202 representative of the bottom portion of the primary tower 90 was stirred in the one liter flask for about 1.5 hours with a monitoring frequency of one data point per minute. The starting solution was a mixture of acetic acid, tively easier analyses) could also be subject to process control. Thus, a compositional profile of the whole tower based on on-line infrared analysis would have implications for optimization of both the purification section and reaction section.

TABLE 17

Addition of Acetic Acid, Vinyl Acetate and Water to Primary Tower Bottoms Type Solution: Correlation of Extended Mid-Infrared Values with Independent Off-Line Analyses (GC/Karl Fischer/Weighing)

| Vinyl Acetate (Molar) | | Acetic Acid (Molar) | | Water (Molar) | | Acetaldehyde (Molar) | | Glycol Diacetate (Molar) | | Polyvinyl Acetate (Wt %) | |
|---|---|---|---|---|---|---|---|---|---|---|---|
| Infrared | GC | Infrared | GC | Infrared | Karl Fischer | Infrared | GC | Infrared | GC | Infrared | Weighing |
| 0 | 0 | 14.43 | 14.34 | 8.49 | 8.50 | 0 | 0 | 0.22 | 0.21 | 0.46 | 0.44 |
| 0.10 | 0.11 | 14.23 | 14.21 | 8.43 | 8.42 | 0.001 | 0 | 0.22 | 0.21 | 0.45 | 0.44 |
| 0.20 | 0.23 | 14.14 | 14.08 | 8.36 | 8.34 | 0.020 | 0 | 0.21 | 0.20 | 0.39 | 0.44 |
| 0.33 | 0.35 | 14 | 13.94 | 8.26 | 8.24 | 0.004 | 0 | 0.21 | 0.20 | 0.41 | 0.43 |
| 0.71 | 0.74 | 13.56 | 13.49 | 8.01 | 7.97 | 0.010 | 0 | 0.20 | 0.20 | 0.41 | 0.42 |
| 0.99 | 1.11 | 13.14 | 13.06 | 7.75 | 7.70 | 0.080 | 0 | 0.18 | 0.19 | 0.37 | 0.40 |
| 1.45 | 1.48 | 12.72 | 12.64 | 7.50 | 7.45 | 0.060 | 0 | 0.17 | 0.18 | 0.38 | 0.39 |
| 1.72 | 1.83 | 12.30 | 12.23 | 7.26 | 7.20 | 0.090 | 0 | 0.17 | 0.18 | 0.34 | 0.38 |
| 2.21 | 2.17 | 11.91 | 11.84 | 7.02 | 6.97 | 0.080 | 0 | 0.16 | 0.17 | 0.36 | 0.36 |

Example 8

Figure 14:
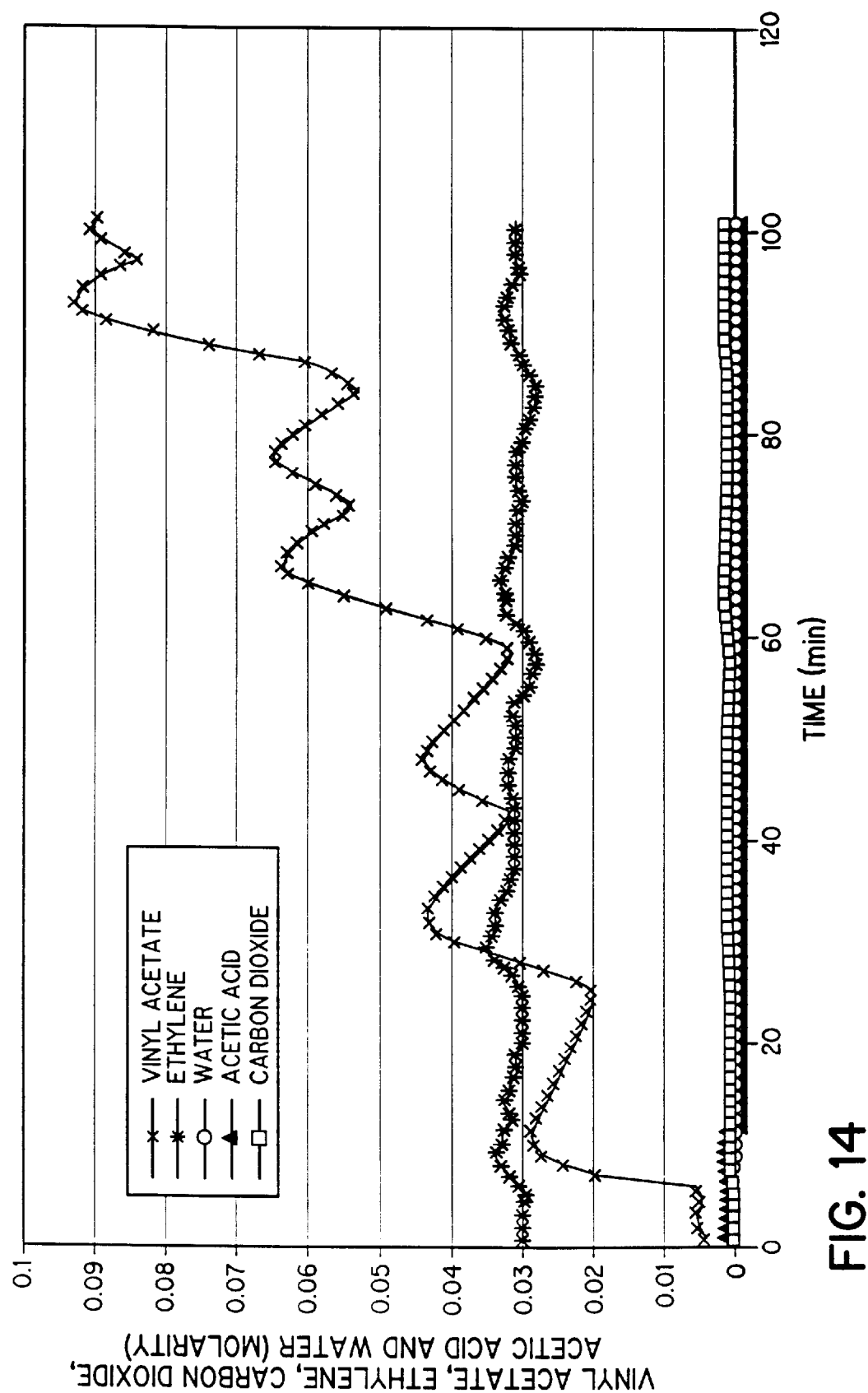
FIG. 14 is a multi-component trend file containing 100 minutes of run time data for five reactor vessel solution components.

Vinyl acetate and ethylene were introduced independently to the gas cell. 0.5 mls of liquid vinyl acetate was first syringed into the cell throughout the ball valve. The cell was then briefly purged with 0.68 atmospheres of gaseous ethylene and all valves closed. This mixture was heated incrementally from room temperature to about 105° C. The temperature was held at 55, 70, 90 and 105° C. for data collection and the cell was monitored continuously using the infrared calibration models developed for reactor inlet and outlet components. The expected behavior was observed as shown in FIG. 14. The ethylene concentration in the vapor phase remained unchanged, while an increase in concentration of vinyl acetate was observed as its vapor pressure increased with temperature. The cyclic or wave behavior of the vinyl acetate trend line at any particular temperature is a function of similar cycling in the cell temperature. There is some oscillation around the temperature set point due to limitations of the laboratory temperature controller. Those skilled in the art of vinyl acetate processing would be aware that appropriately sized heaters and controllers in a manufacturing plant would not have such limitations. The average vinyl acetate concentration at each set point was calculated and is shown in Table 18 where the values for vapor phase concentrations are compared with the values predicted from the ideal gas equation. The data in this table show good agreement between the values calculated from the ideal gas equation and values predicted by the infrared calibration model. Table 18 and FIG. 14 also show negligible false positive readings for carbon dioxide, water and acetic acid, all of which were present at zero concentration in this experiment.

Example 9

Figure 15:
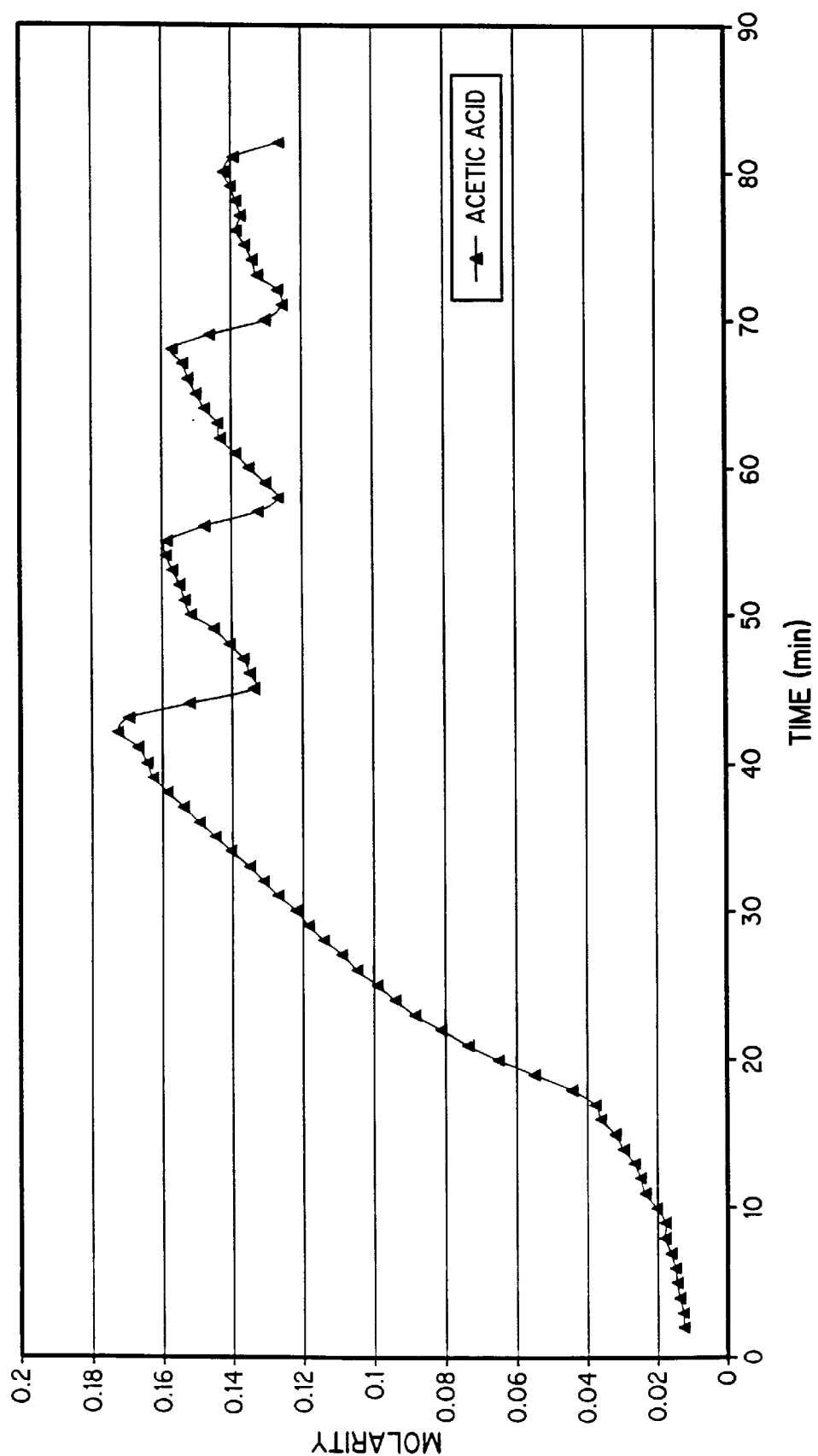
FIG. 15 is a single-component trend file containing 80 minutes of run time date for acetic acid in the reactor vessel.

One mL of acetic acid was added to the gas cell at room temperature. The cell was then heated in one stage over about 40 minutes to about 180° C. as shown in FIG. 15. The cell was held at this temperature for a further 40 minutes. The cell was monitored continuously over both time periods by infrared. Based on the vapor pressure curve of acetic acid referred to earlier and on a calculation using the ideal gas equation, the expected vapor phase concentration at 180° C. is 0.135 molar. Due to the temperature controller limitations referred to in the previous example, the temperature initially overshoots and the vapor phase concentration as predicted by the acetic acid calibration model reaches 0.17 molar. As shown in FIG. 15, the average acetic acid concentration associated with each cycle in temperature decreases towards the expected value of 0.135 molar as the temperature settles into its target value. Thus, the smoothness of the acetic acid trend line associated with the fairly rapid smooth rise in temperature, the ability of the calibration model to pick up small cyclic changes in acetic acid vapor phase concentration and the good agreement between the predicted and actual acetic acid concentration at the set temperature are all indicative of a high degree of accuracy and precision with regard to acetic acid vapor phase measurement.

Example 10

The experiment outlined in this example demonstrates the feasibility of measurement of all five gaseous components simultaneously. 0.072 mls of vinyl acetate, 0.040 mls of water and 0.150 mls of acetic acid were added to the gas cell via syringe at room temperature. Approximately 0.05 grams of dry ice was quickly added through the ball valve and

TABLE 18

Temperature Profile of a Mixture of Ethylene and Vinyl Acetate: Correlation of On-Line Extended Mid-Infrared Values with Values Predicted from the Ideal Gas Equation

Figure 16:
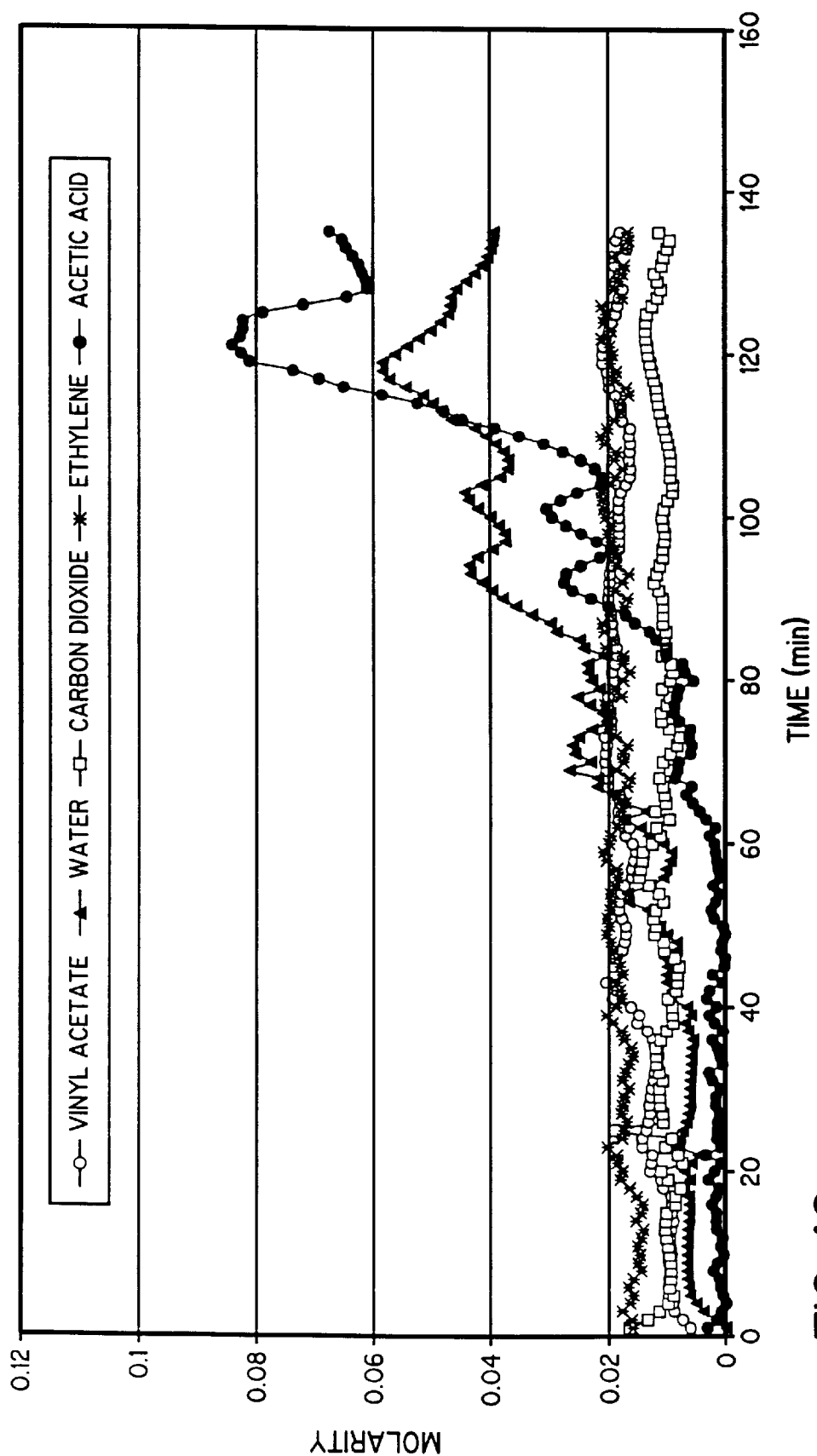
FIG. 16 is a multi-component trend file containing 135 minutes of run time data for five reactor vessel gaseous components.

| Temperature (° C.) | Ethylene (Molar) | | Vinyl Acetate (Molar) | | Water (Molar) | | Carbon Dioxide (Molar) | | Acetic Acid (Molar) | |
|---|---|---|---|---|---|---|---|---|---|---|
| | Infrared | Equation | Infrared | Equation | Infrared | Equation | Infrared | Equation | Infrared | Equation |
| 21 | 0.030 | 0.028 | 0.004 | 0.005 | 0 | 0 | 0.0002 | 0 | 0.0007 | 0 |
| 55 | 0.032 | 0.028 | 0.020 | 0.024 | 0 | 0 | 0.0004 | 0 | 0.0008 | 0 |
| 70 | 0.031 | 0.028 | 0.031 | 0.037 | 0 | 0 | 0.0008 | 0 | 0 | 0 |
| 90 | 0.030 | 0.028 | 0.053 | 0.058 | 0 | 0 | 0.0009 | 0 | 0 | 0 |
| 105 | 0.032 | 0.028 | 0.085 | 0.086 | 0 | 0 | 0.0011 | 0 | 0 | 0 | finally 0.5 atmospheres of ethylene was added with a purge of a few seconds. The cell was then heated in six increments up to 180° C. over a two-hour period with continuous monitoring by infrared. Because of the complexities of determining the partial vapor pressures of all components at different temperatures, no attempt was made to do so. However, those skilled in the art of vapor phase chemistry and non-ideality are aware that many commercial software packages exist that allow individual vapor liquid equilibria in mixtures to be calculated. Examples of such software packages include ASPEN® (Aspentech, Cambridge, Mass.) and Simulation Sciences (Simulation Sciences Inc., Brea, Calif.). Trend lines for all five components are shown in FIG. 16. The anticipated trends are observed. Carbon dioxide and ethylene, which are both entirely in the gaseous state at room temperature and which have negligible solubility in the liquid components, show essentially no change in concentration over the course of the experiment. Vinyl acetate, which has a considerably lower boiling point and higher vapor pressure than acetic acid or water, is converted entirely into the gaseous state over a shorter time period (lower temperature) than acetic acid and water. Acetic acid and water, with relatively similar boiling points, show relatively similar trend line behavior as shown in FIG. 16. Thus, this experiment demonstrates the feasibility of quantitative analysis of a gaseous mixture containing carbon dioxide, ethylene, acetic acid, water and vinyl acetate.

The above discussion demonstrates that process control of component concentrations for optimization of the manufacture and purification of vinyl acetate product may be effected by infrared measurements of component concentrations in samples collected continuously from locations in the reaction system at and downstream of the reactor vessel, with immediate responsive adjustments made in component concentrations, whether directly or indirectly, at an appropriate location in the reaction system. The reaction system includes numerous columns and streams, each of which when fitted with the appropriate monitoring equipment can provide concentration information that informs the system operator where adjustments are needed. The system operator may be an individual or a computerized control system. In other words, the process control can be either manual or automatic. Because the measurements in the process control of the present invention are continuously taken, such as at 30 second to 3 minute intervals, followed by substantially instant adjustment of some process variable in the reaction system, the system operator would advantageously be a computerized control unit that analyzes the incoming data from the infrared analyzer, comparing it to known control limits set for the process variables, and automatically effects the appropriate adjustments to maximize the production of pure vinyl acetate. Alternatively, the data may be fed to a display unit to be interpreted by an individual who adjusts reaction system components or process variables manually. The adjustments, as stated above, may directly or indirectly alter the concentration of one or more components in one or more locations in the reaction system. Direct adjustment may occur by adding or extracting a component at a location in the reaction system. Indirect adjustment of component concentrations may occur in any number of ways. For example, adjusting the temperature of a solution or the temperature profile in a column affects component concentrations. Decreasing or increasing flow rates of streams from one vessel to another affects component concentrations, not just in those vessels, but may also affect concentrations in other vessels throughout the reaction system. There are many relationships between the different components comprising the solutions in the different locations of the reaction system, as understood by one skilled in the art, and the adjustment of one component concentration at one location in the reaction system can have an effect on more than one component concentration at more than one location in the reaction system. Thus, real time infrared measurement, analysis and adjustment is used in the present invention to control a vinyl acetate manufacturing process so as to maximize the efficiency and output of the reaction system.

While the present invention has been illustrated by the description of embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatuses and methods and illustrative examples shown and described. Accordingly, departures may be made from such details without departing from the scope or spirit of applicant's general inventive concept.

What is claimed is:

1. A method of effecting process control of component concentrations in a reaction system for the production of vinyl acetate from the oxidation of ethylene and acetic acid, the method comprising the steps of:

collecting a reaction system sample comprising at least one component selected from the group consisting of water, oxygen, vinyl acetate, acetic acid, carbon dioxide, ethylene, ethanol, methyl acetate, ethyl acetate, glycol diacetate, polyvinyl acetate, acetaldehyde, acetone, acrolein, polymerization inhibitor, potassium carbonate, potassium bicarbonate, potassium acetate, and potassium hydroxide;

measuring the concentration of at least one of said components in said sample in an infrared analyzer; and adjusting a component concentration in the reaction system in response to the measured concentration.

2. The method of claim 1 wherein the adjusting is accomplished directly by adding or removing a component from at least one of a reactor vessel, a column downstream of the reactor vessel or a transfer line downstream of the reactor vessel in the reaction system in response to the measured concentration.

3. The method of claim 1 wherein the adjusting is accomplished indirectly by adjusting in at least one of a reactor vessel, a column downstream of the reactor vessel or a transfer line downstream of the reactor vessel in the reaction system at least one of a temperature of a reaction system solution, a temperature profile in the column, a flow rate of a reaction system solution and a vent gas rate.

4. The method of claim 1 comprising collecting the sample from each of a feed and an effluent of a reactor vessel in the reaction system, and measuring in the infrared analyzer the concentration of at least one of vinyl acetate, acetic acid, carbon dioxide and ethylene, and adjusting at least one of the following in response to the measured concentration of vinyl acetate, acetic acid, carbon dioxide or ethylene:

a. the temperature of the feed to the reactor vessel;
b. the flow rate of the feed to the reactor vessel;
c. the composition of the feed to the reactor vessel;
d. the flow rate of a reactor coolant;
e. the temperature of the reactor coolant.

5. The method of claim 1 comprising collecting the sample from a combined stream from a bottom stream of an absorber and a bottom stream of a scrubber, measuring in the infrared analyzer the concentrations of at least one of vinyl acetate and acetic acid, and adjusting at least one of the following in response to the measured concentration of vinyl acetate or acetic acid:
   a. the temperature of a primary tower bottoms stream to the absorber;
   b. the flow rate of the primary tower bottoms stream to the absorber;
   c. the flow rate of the combined stream to the primary tower.

6. The method of claim 1 comprising collecting the sample from a bottom of a carbon dioxide absorber, measuring in the infrared analyzer the concentration of at least one of potassium carbonate, potassium bicarbonate and potassium acetate in the bottom, and adjusting the rate of blowdown of the carbon dioxide absorber bottoms in response to the measured concentration of potassium carbonate, potassium bicarbonate or potassium acetate.

7. The method of claim 1 comprising collecting the sample from an overhead of a carbon dioxide stripper, measuring in the infrared analyzer the concentration of carbon dioxide in the overhead, and adjusting the injection rate of potassium hydroxide to the carbon dioxide absorber in response to the measured concentration of carbon dioxide.

8. The method of claim 1 comprising collecting the sample from a feed stream and a vent stream of an ethylene recovery unit, measuring in the infrared analyzer the concentration of ethylene, and adjusting at least one of the flow rate of the feed stream to the ethylene recovery unit and the flow rate of a vinyl acetate stream to the ethylene recovery unit in response to the measured concentration of ethylene.

9. The method of claim 1 comprising collecting the sample from a bottom waste stream from an acid recovery unit, measuring in the infrared analyzer the concentration of acetic acid, and adjusting the vacuum on the acid recovery unit in response to the measured concentration of acetic acid.

10. The method of claim 1 comprising collecting a profile of liquid samples from an acid tower, measuring in the infrared analyzer the concentration of at least one of acetic acid, water, glycol diacetate and polyvinyl acetate, and adjusting at least one of the following in response to the measured concentration of acetic acid, water, glycol diacetate or polyvinyl acetate:
   a. the flow rate to an acid recovery unit;
   b. the acetic acid content of a feed to the acid tower;
   c. the boilup of the acid tower.

11. The method of claim 1 comprising collecting a profile of liquid samples in a primary tower, measuring in the infrared analyzer the concentration of at least one of acetic acid, water, vinyl acetate, ethyl acetate and polyvinyl acetate, and adjusting at least one of the following in response to the measured concentration of acetic acid, water, vinyl acetate, ethyl acetate or polyvinyl acetate:
   a. the temperature of the primary tower bottoms;
   b. the flow rate of demineralized water to a scrubber;
   c. the flow rate of a stream to the primary tower;
   d. the reflux to the primary tower;
   e. the boilup of the primary tower;
   f. the injection rate of polymerization inhibitor to a decanter;
   g. the flow rate of a sidedraw stream from the primary tower to an ethyl acetate tower.

12. The method of claim 1 comprising collecting the sample from both liquid phases of a decanter associated with a primary tower, measuring in the infrared analyzer the concentration of at least one of acetic acid, acetaldehyde, vinyl acetate and water, and adjusting at least one of the following in response to the measured concentration of acetic acid, acetaldehyde, vinyl acetate or water:
   a. the temperature of the decanter;
   b. the temperature of a water stripper bottoms;
   c. the temperature of a drying column bottoms;
   d. the reflux to the primary tower;
   e. the feed to the drying column;
   f. the feed to the water stripper.

13. The method of claim 1 comprising collecting the sample from at least one of a feed, bottoms and overhead of a drying column, measuring in the infrared analyzer the concentration of at least one of vinyl acetate and water, and adjusting the drying column bottoms temperature in response to the measured concentration of vinyl acetate or water.

14. The method of claim 1 comprising collecting the sample from at least one of a feed, bottoms and overhead of a drying tower, measuring in the infrared analyzer the concentration of polyvinyl acetate, and adjusting the injection rate of polymerization inhibitor to a decanter in response to the measured concentration of polyvinyl acetate.

15. The method of claim 1 comprising collecting the sample from a liquid in a lights tower reflux drum and from trays of a lights tower, measuring in the infrared analyzer the concentration of at least one of vinyl acetate, acetone, acrolein, acetaldehyde, ethanol and methyl acetate, and adjusting at least one of the boilup of the lights tower and a purge rate from the lights tower reflux drum in response to the measured concentrations of vinyl acetate, acetone, acrolein, acetaldehyde, ethanol or methyl acetate.

16. The method of claim 1 comprising collecting the sample from at least one of a condensed overhead liquid of a product tower, a liquid from trays of the product tower, and a liquid from bottoms of the product tower, measuring in the infrared analyzer the concentration of vinyl acetate, and adjusting the temperature profile of the product tower in response to the measured concentration of vinyl acetate.

17. The method of claim 1 comprising collecting the sample from at least one of a condensed overhead liquid of a product tower, a liquid from trays of the product tower, and a liquid from bottoms of the product tower, measuring in the infrared analyzer the concentration of at least one of ethyl acetate and polyvinyl acetate, and adjusting at least one of the following in response to the measured concentration of ethyl acetate or polyvinyl acetate:
   a. the reflux flow to the product tower;
   b. the flow rate of the product tower bottoms to a product recovery unit;
   c. the injection rate of polymerization inhibitor to a product tower reflux drum.

18. The method of claim 1 comprising collecting the sample from a heavy waste stream from a product recovery unit, measuring in the infrared analyzer the concentration of at least one of vinyl acetate and ethyl acetate, and adjusting at least one of the flow rate of a product tower bottoms to the product recovery unit and the recycle rate from the product recovery unit to the product tower in response to the measured concentration of vinyl acetate or ethyl acetate.

19. The method of claim 1 further comprising transmitting the measured concentrations to a control unit for real time analysis.

20. The method of claim 19 wherein the adjusting is substantially instantly after the measuring and analysis.

21. The method of claim 1 wherein the measuring and adjusting is performed about every 30 seconds to 3 minutes.

22. The method of claim 1 wherein the infrared analyzer is a Fourier Transform infrared spectrometer.

* * * * *